(12) United States Patent
Salman et al.

(10) Patent No.: US 10,517,464 B2
(45) Date of Patent: *Dec. 31, 2019

(54) MULTI-ELEMENT COVER FOR A MULTI-CAMERA ENDOSCOPE

(71) Applicant: EndoChoice, Inc., Alpharetta, GA (US)

(72) Inventors: Golan Salman, Atlit (IL); Amram Aizenfeld, Ramot Menashe (IL); Jeruham Avron, Haifa (IL)

(73) Assignee: EndoChoice, Inc., Alpharetta, GA (US)

(*) Notice: Subject to any disclaimer, the term of this patent is extended or adjusted under 35 U.S.C. 154(b) by 336 days.

This patent is subject to a terminal disclaimer.

(21) Appl. No.: 15/411,103

(22) Filed: Jan. 20, 2017

(65) Prior Publication Data
US 2017/0127914 A1    May 11, 2017

Related U.S. Application Data

(63) Continuation-in-part of application No. 15/144,569, filed on May 2, 2016, now Pat. No. 10,070,774, (Continued)

(51) Int. Cl.
*A61B 1/04* (2006.01)
*A61B 1/00* (2006.01)
(Continued)

(52) U.S. Cl.
CPC ........ *A61B 1/00096* (2013.01); *A61B 1/0011* (2013.01); *A61B 1/00091* (2013.01);
(Continued)

(58) Field of Classification Search
CPC . A61B 1/00096; A61B 1/00101; A61B 1/053; A61B 1/0676; A61B 1/0615; A61B 1/00091; A61B 1/018; A61B 1/00137
(Continued)

(56) References Cited

U.S. PATENT DOCUMENTS 3,639,714 A    2/1972    Fujimoto
3,955,064 A    5/1976    Demetrio
(Continued)

FOREIGN PATENT DOCUMENTS

CA    2297986    3/1999
CA    2765559    12/2010
(Continued)

OTHER PUBLICATIONS

International Search Report for PCT/US2017/014263, dated Apr. 10, 2017.
(Continued)

*Primary Examiner* — Matthew J Kasztejna
(74) *Attorney, Agent, or Firm* — Bookoff McAndrews, PLLC

(57) ABSTRACT

A multi-camera endoscope includes a the tip section comprising: a front looking camera and a front discrete illuminator to essentially illuminate the field of view of said front looking camera; a right side looking camera and a right discrete illuminator to essentially illuminate the field of view of said right side looking camera; a left side looking camera and a left discrete illuminator to essentially illuminate the field of view of said left side looking camera; and a multi-component cover configured to cover and seal said tip section such as to essentially prevent entry of fluids from the environment of said endoscope to inner parts of said tip section. The tip cover includes removable or repositionable window components which provide access to internal components of the tip for repair or removal, without removing the main tip cover.

20 Claims, 17 Drawing Sheets

Related U.S. Application Data which is a continuation of application No. 14/791,314, filed on Jul. 3, 2015, now Pat. No. 9,351,629, which is a continuation of application No. 13/984,028, filed as application No. PCT/IL2012/050037 on Feb. 6, 2012, now Pat. No. 9,101,266.

(60) Provisional application No. 62/286,772, filed on Jan. 25, 2016, provisional application No. 61/439,948, filed on Feb. 7, 2011.

(51) Int. Cl.
    *A61B 1/06* (2006.01)
    *A61B 1/05* (2006.01)
    *A61B 1/12* (2006.01)
    *G02B 23/24* (2006.01)
    *G02B 27/00* (2006.01)

(52) U.S. Cl.
    CPC ...... *A61B 1/00137* (2013.01); *A61B 1/00142* (2013.01); *A61B 1/00177* (2013.01); *A61B 1/00181* (2013.01); *A61B 1/051* (2013.01); *A61B 1/0615* (2013.01); *A61B 1/0676* (2013.01); *A61B 1/0684* (2013.01); *A61B 1/126* (2013.01); *G02B 23/2476* (2013.01); *G02B 27/0006* (2013.01); *G02B 23/2423* (2013.01)

(58) Field of Classification Search
    USPC ........ 600/109, 113, 129–130, 156, 157, 165, 600/170–171
    See application file for complete search history.

(56) References Cited

U.S. PATENT DOCUMENTS

| | | | |
|---|---|---|---|
| 4,027,697 | A | 6/1977 | Bonney |
| 4,037,588 | A | 7/1977 | Heckele |
| 4,084,401 | A | 4/1978 | Belardi |
| 4,402,313 | A | 9/1983 | Yabe |
| 4,461,282 | A | 7/1984 | Ouchi |
| 4,494,549 | A | 1/1985 | Namba |
| 4,532,918 | A | 8/1985 | Wheeler |
| 4,588,294 | A | 5/1986 | Siegmund |
| 4,641,635 | A | 2/1987 | Yabe |
| 4,727,859 | A | 3/1988 | Lia |
| 4,764,001 | A | 8/1988 | Yokota |
| 4,801,792 | A | 1/1989 | Yamasita |
| 4,825,850 | A | 5/1989 | Opie |
| 4,877,314 | A | 10/1989 | Kanamori |
| 4,902,115 | A | 2/1990 | Takahashi |
| 4,976,522 | A | 12/1990 | Igarashi |
| 4,984,878 | A | 1/1991 | Miyano |
| 5,007,406 | A | 4/1991 | Takahashi |
| 5,014,685 | A | 5/1991 | Takahashi |
| 5,193,525 | A | 3/1993 | Silverstein |
| 5,224,929 | A | 7/1993 | Remiszewski |
| 5,296,971 | A | 3/1994 | Mori |
| 5,359,456 | A | 10/1994 | Kikuchi |
| 5,395,329 | A | 3/1995 | Fleischhacker |
| 5,447,148 | A | 9/1995 | Oneda |
| 5,460,167 | A | 10/1995 | Yabe |
| 5,464,007 | A | 11/1995 | Krauter |
| 5,475,420 | A | 12/1995 | Buchin |
| 5,489,256 | A | 2/1996 | Adair |
| 5,518,501 | A | 5/1996 | Oneda |
| 5,518,502 | A | 5/1996 | Kaplan |
| 5,547,455 | A | 8/1996 | McKenna |
| 5,547,457 | A | 8/1996 | Tsuyuki |
| 5,575,755 | A | 11/1996 | Krauter |
| 5,587,839 | A | 12/1996 | Miyano |
| 5,630,782 | A | 5/1997 | Adair |
| 5,630,798 | A | 5/1997 | Beiser |
| 5,662,588 | A | 9/1997 | Iida |
| 5,674,182 | A | 10/1997 | Suzuki |
| 5,685,821 | A | 11/1997 | Pike |
| 5,685,823 | A | 11/1997 | Ito |
| 5,702,347 | A | 12/1997 | Yabe |
| 5,707,344 | A | 1/1998 | Nakazawa |
| 5,725,474 | A | 3/1998 | Yasui |
| 5,725,476 | A | 3/1998 | Yasui |
| 5,725,477 | A | 3/1998 | Yasui |
| 5,725,478 | A | 3/1998 | Saad |
| 5,777,797 | A | 7/1998 | Miyano |
| 5,782,751 | A | 7/1998 | Matsuno |
| 5,800,341 | A | 9/1998 | McKenna |
| 5,810,715 | A | 9/1998 | Moriyama |
| 5,810,717 | A | 9/1998 | Maeda |
| 5,810,770 | A | 9/1998 | Chin |
| 5,830,121 | A | 11/1998 | Enomoto |
| 5,836,894 | A | 11/1998 | Sarvazyan |
| 5,860,913 | A | 1/1999 | Yamaya |
| 5,870,234 | A | 2/1999 | EbbesmeierneeSchitthof |
| 5,916,148 | A | 6/1999 | Tsuyuki |
| 5,940,126 | A * | 8/1999 | Kimura ............... H04N 5/2253 348/294 |
| 6,058,109 | A | 5/2000 | Lechleider |
| 6,095,970 | A | 8/2000 | Hidaka |
| 6,095,971 | A | 8/2000 | Takahashi |
| 6,117,068 | A | 9/2000 | Gourley |
| 6,181,481 | B1 | 1/2001 | Yamamoto |
| 6,196,967 | B1 | 3/2001 | Lim |
| 6,261,226 | B1 | 7/2001 | McKenna |
| 6,277,064 | B1 | 8/2001 | Yoon |
| 6,359,674 | B1 | 3/2002 | Horiuchi |
| 6,375,610 | B2 | 4/2002 | Verschuur |
| 6,402,738 | B1 | 6/2002 | Ouchi |
| 6,419,626 | B1 | 7/2002 | Yoon |
| 6,476,851 | B1 | 11/2002 | Nakamura |
| 6,520,908 | B1 | 2/2003 | Ikeda |
| 6,605,035 | B2 * | 8/2003 | Ando ............... A61B 1/0008 600/127 |
| 6,636,254 | B1 | 10/2003 | Onishi |
| 6,638,214 | B2 | 10/2003 | Akiba |
| 6,673,012 | B2 | 1/2004 | Fujii |
| 6,690,337 | B1 | 2/2004 | Mayer, III |
| 6,712,760 | B2 | 3/2004 | Sano |
| 6,832,984 | B2 | 12/2004 | Stelzer |
| 6,888,119 | B2 | 5/2005 | Iizuka |
| 6,997,871 | B2 | 2/2006 | Sonnenschein |
| 7,154,378 | B1 | 12/2006 | Ertas |
| 7,371,209 | B2 * | 5/2008 | Viebach ............... A61B 1/0008 600/102 |
| 7,435,218 | B2 | 10/2008 | Krattiger |
| 7,621,869 | B2 | 11/2009 | Ratnakar |
| 7,630,148 | B1 | 12/2009 | Yang |
| 7,701,650 | B2 | 4/2010 | Lin |
| 7,713,246 | B2 | 5/2010 | Shia |
| 7,746,572 | B2 | 6/2010 | Asami |
| 7,813,047 | B2 | 10/2010 | Wang |
| 7,828,725 | B2 | 11/2010 | Maruyama |
| 7,918,788 | B2 | 4/2011 | Lin |
| 7,927,272 | B2 | 4/2011 | Bayer |
| 7,967,745 | B2 | 6/2011 | Gilad |
| 7,976,462 | B2 | 7/2011 | Wright |
| 8,064,666 | B2 | 11/2011 | Bayer |
| 8,182,422 | B2 | 5/2012 | Bayer |
| 8,197,399 | B2 | 6/2012 | Bayer |
| 8,235,887 | B2 | 8/2012 | Bayer |
| 8,262,558 | B2 | 9/2012 | Sato |
| 8,287,446 | B2 | 10/2012 | Bayer |
| 8,289,381 | B2 | 10/2012 | Bayer |
| 8,300,325 | B2 | 10/2012 | Katahira |
| 8,310,530 | B2 | 11/2012 | Bayer |
| 8,353,860 | B2 | 1/2013 | Boulais |
| 8,447,132 | B1 | 5/2013 | Galil |
| 8,449,457 | B2 | 5/2013 | Aizenfeld |
| 8,460,182 | B2 | 6/2013 | Ouyang |
| 8,585,584 | B2 | 11/2013 | Ratnakar |
| 8,587,645 | B2 | 11/2013 | Bayer |
| 8,672,836 | B2 | 3/2014 | Higgins |
| 8,715,168 | B2 | 5/2014 | Ratnakar |

(56) References Cited

U.S. PATENT DOCUMENTS

| | | |
|---|---|---|
| 8,797,392 B2 | 8/2014 | Bayer |
| 8,870,753 B2 * | 10/2014 | Boulais .............. A61B 1/0008 600/129 |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0182299 A1 * | 8/2005 | D'Amelio .......... A61B 1/00096 600/175 |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Gamer |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |

(56) References Cited

U.S. PATENT DOCUMENTS

| | | |
|---|---|---|
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |

(56) References Cited

FOREIGN PATENT DOCUMENTS

| | | |
|---|---|---|
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11-137512 * | 5/1999 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.otonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.

(56) References Cited

OTHER PUBLICATIONS

Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report for PCT/US14/37004, dated Sep. 25, 2014.
International Search Report for PCT/US14/38094, dated Nov. 6, 2014.
International Search Report for PCT/US2014/037526, dated Oct. 16, 2014.
International Search Report for PCT/US2014/071085, dated Mar. 27, 2015.
International Search Report for PCT/US2014/58143, dated Jan. 21, 2015.
International Search Report for PCT/US2015/012506, dated Dec. 11, 2015.
International Search Report for PCT/US2015/012751, dated Jun. 26, 2015.
International Search Report for PCT/US2015/027902, dated Jul. 23, 2015.
International Search Report for PCT/US2015/28962, dated Jul. 28, 2015.
International Search Report for PCT/US2015/29421, dated Aug. 7, 2015.
International Search Report for PCT/US2015/41396, dated Sep. 29, 2015.
International Search Report for PCT/US2015/47334, dated Dec. 28, 2015.
International Search Report for PCT/US2015/6548, dated Feb. 26, 2016.
International Search Report for PCT/US2015/66486, dated Dec. 17, 2015.

\* cited by examiner

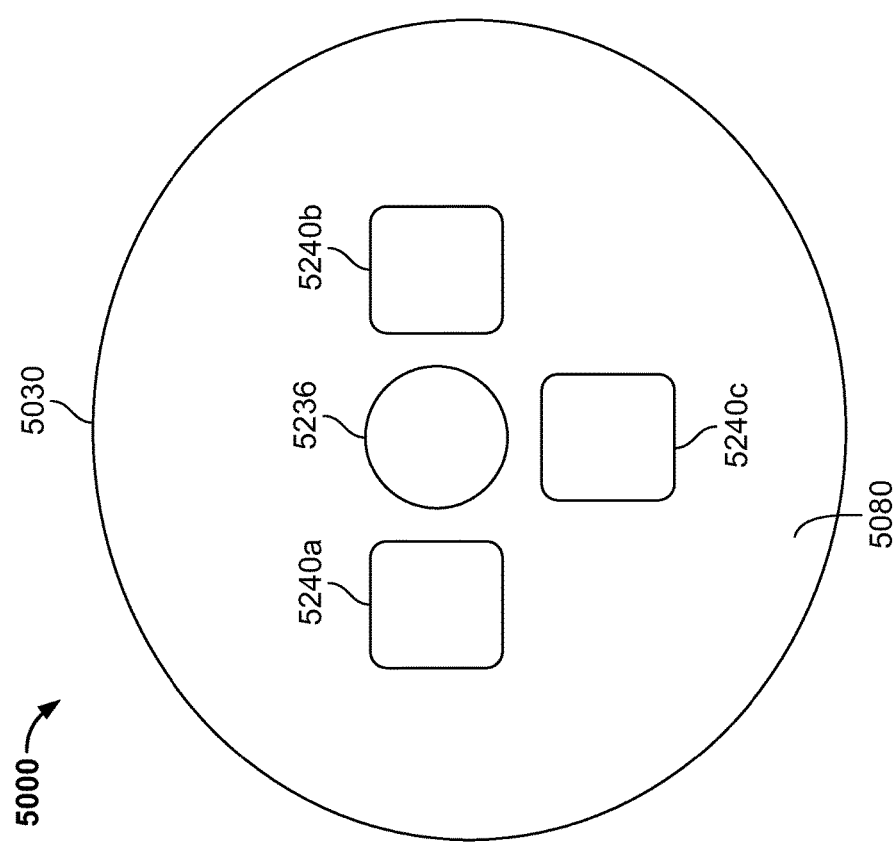

MULTI-ELEMENT COVER FOR A MULTI-CAMERA ENDOSCOPE

CROSS-REFERENCE

The present application relies on U.S. Provisional Patent Application No. 62/286,772, entitled "Multi-Element Cover for a Multi-Camera Endoscope" and filed on Jan. 25, 2016, for priority, which is herein incorporated by reference in its entirety.

The present application is also a continuation-in-part application of U.S. patent application Ser. No. 15/144,569, entitled "Multi-Element Cover for a Multi-Camera Endoscope" and filed on May 2, 2016, which is a continuation application of U.S. patent application Ser. No. 14/791,314, of the same title, filed on Jul. 3, 2015, and issued as U.S. Pat. No. 9,351,629 on May 31, 2016, which, in turn, is a continuation application of U.S. patent application Ser. No. 13/984,028, of the same title, filed on Aug. 22, 2013, and issued as U.S. Pat. No. 9,101,266 on Aug. 11, 2015, which is a national stage entry application of PCT Application Number PCT/IL2012/050037, entitled "Multi-Element Cover for a Multi-Camera Endoscope" and filed on Feb. 6, 2012, which relies on U.S. Provisional Patent Application No. 61/439,948, filed on Feb. 7, 2011 for priority. All of the aforementioned applications are herein incorporated by reference in their entirety.

FIELD

Embodiments of the disclosure relate to a multiple element cover to a tip section of a multi-camera endoscope.

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and sometimes also the illuminator, and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Among the disadvantages of such endoscopes are their limited field of view and their complicated packing of all the required elements, such as electronics and fiber optics together with fluid carrying elements, in the small sized endoscope tip section. Another problem with existing endoscopes is the difficult assembling of the gentle electronic components, which are often damaged by the assembling process itself. Another problem with existing endoscopes is the complicated sealing of the parts, specifically in the tip section of the endoscope. Sealing of the tip section remains a challenge particularly due to the complex environment in which the endoscope is intended to operate.

There is thus a need in the art for endoscopes, such as colonoscopes, that allow a broader field of view and also enable efficient packing, assembling and sealing of all necessary elements in the tip section while maintaining their function.

SUMMARY

The following embodiments and aspects thereof are described and illustrated in conjunction with systems, tools and methods which are meant to be exemplary and illustrative, not limiting in scope.

In some embodiments, the present specification discloses a multi-component cover for the tip section of a multi-viewing element endoscope, said tip section comprising a front pointing viewing element and at least one side pointing viewing element, wherein each viewing element comprises an image sensor and a lens assembly, and each viewing element is associated with a discrete illuminator, said multi-component cover comprising: a main component configured to cover a portion of said tip section, wherein said main component has a total surface area; and a removable window component located on a side surface panel of said main component wherein said removable window component has a surface area that is equal to 30 to 85% of said total surface area of said main component, said removable window component configured to removably cover a window opening located on said main component, wherein said window opening is positioned to allow access to an inner part of said tip section without removing said main component.

Optionally, said window opening is located on said side surface panel such that it aligns with said removable window component.

Optionally, said window opening has edges that are adapted to couple to the removable window component.

Optionally, said window opening is aligned with at least one of: said side pointing viewing element; an optical assembly of said side pointing viewing element; a side discrete illuminator; and a side nozzle.

Optionally, said windows are aligned such that a distance from said windows to the underlying side pointing viewing element or side discrete illuminator is in a range of 0 to 3 millimeters.

Optionally, the multi-component cover further comprises a removable window component positioned on a front end of the main component of said tip cover, said front removable component being configured to cover a front window opening which allows access to a front inner part of said tip section. Optionally, said front removable window component comprises a window for at least one of: said front pointing viewing element; an optical assembly of said front pointing viewing element; a front discrete illuminator; a working/service channel; a front nozzle; and a front jet. Still optionally, said window of the front removable window component is aligned such that a distance from said window of the front removable window component to the front pointing viewing element or front discrete illuminator is in a range of 0 to 3 millimeters.

Optionally, the main component further includes a groove on a side surface, said groove being configured to allow the removable window component to slide along the groove and be repositioned on, or removed from, the multi-component cover.

Optionally, the removable window component comprises a flat surface to assist in directing a cleaning fluid injected from an injector channel towards a side optical assembly and optical windows.

Optionally, said tip section has a diameter of 17 mm or less.

Optionally, said main component is cylindrical in shape and has a diameter ranging between 2 mm and 17 mm.

Optionally, said removable window component comprises a flat depression having openings for accessing a side optical lens assembly, side illuminators and a side nozzle.

Optionally, said window opening is positioned on a circumference of said main component at a distance of 1 to 9 mm from a front surface of said main component.

Optionally, said window opening is positioned on a circumference of said main component at a distance of 7 mm to 7.9 mm from a front surface of said main component.

In some embodiments, the present specification discloses a tip section of a multi-camera endoscope, the tip section comprising: a front looking camera and a front discrete illuminator to essentially illuminate a field of view of said front looking camera; a first side looking camera and a first side discrete illuminator to essentially illuminate a field of view of said side looking camera, and a multi-component cover configured to cover and seal said tip section comprising a main component configured to cover a majority of said tip section; a first side removable component coupled to a side surface portion of said main component and having a surface area, said surface area being 30 to 85% of a surface area of said main component, wherein said first side removable component is configured to removably cover an opening located on said main component and wherein said opening is positioned to allow access to an inner part of said tip section without removing said main component.

Optionally, said tip section further comprises a second side looking camera and a second side discrete illuminator to essentially illuminate the field of view of said second side looking camera and said multi-component cover further comprises a second side removable component coupled to a side surface portion of said main component on an opposite side of said first side removable component and wherein said second side removable component is configured to cover a second opening located on said main component and wherein said second opening is configured to allow access to an inner part of said tip section without removing said main component, further wherein, when said first and second side removable window components are in place on said main component, a distance from a plurality of windows of said side removable window components to said first and second side looking cameras and said first and second side discrete illuminators respectively, is in a range of 0 to 3 millimeters.

Optionally, said multi-component cover further comprises a front removable component configured to cover an opening located on the front portion of said main component and wherein said opening on the front portion is configured to allow access to the inner part of the front panel of said tip section without removing said main component, further wherein when said front side removable window component is in place on said main component, a distance from a plurality of windows of the front removable window component to said front looking camera and front discrete illuminator is in a range of 0 to 3 millimeters.

Optionally, said main component comprises a channel alongside said side removable component and said side removable component is configure to be longitudinally pushed and slid through said channel to be repositioned in open position in which the inner parts of the tip section can be accessed through said opening.

Optionally, said main component comprises a groove alongside said side removable component and said side removable component is configured to be longitudinally pushed and slid through said groove to detach from said main component.

According to some embodiments, there is provided a tip section of a multi-camera endoscope, the tip section comprising: a front-pointing camera and a discrete front illuminator associated therewith; one or more side-pointing cameras and one or more discrete side illuminators associated therewith; and a multi-component cover configured to cover the inner parts of the tip section.

According to some embodiments, there is provided a tip section of a multi-camera endoscope, the tip section comprising: a front looking camera and a front discrete illuminator to essentially illuminate the Field Of View (FOV) of said front looking camera; a side looking camera and a discrete illuminator to essentially illuminate the FOV of said side looking camera, and a multi component cover configured to cover and seal said tip section such as to essentially prevent entry of fluids from the environment of said endoscope to inner parts of said tip section.

According to some embodiments, there is provided a tip section of a multi-camera endoscope, the tip section comprising: a front looking camera and a front discrete illuminator to essentially illuminate the Field Of View (FOV) of the front looking camera; a right side looking camera and a right discrete illuminator to essentially illuminate the FOV of the right side looking camera; a left side looking camera and a left discrete illuminator to essentially illuminate the FOV of the left side looking camera; and a multi-component cover configured to cover and seal the tip section such as to essentially prevent entry of fluids from the environment of the endoscope to inner parts of the tip section.

According to some embodiments, the multi-component cover comprises: a front-side component configured to cover a front part and a side part of the tip section; and a side component configured to cover another side part of the tip section, wherein the front-side component and the side component are configured to abut to cover the tip section. The front-side component may be configured to cover the front part and a right side part of the tip section and the side component is configured to cover a left side part of the tip section. Alternatively, the front-side component may be configured to cover the front part and a left side part of the tip section and the side component is configured to cover a right side part of the tip section.

According to some embodiments, the multi-component cover comprises: a front component configured to cover a front part; a right side component configured to cover a right side part of the tip section; and a left side component configured to cover a left side part of the tip section; wherein the front, right side and left side components are configured to abut to cover the tip section.

According to some embodiments, the multi-component cover comprises: a main component configured to cover the majority of the tip section; and a removable window component configured to cover a window opening located on the main component, wherein the removable window component is configured to allow access to an inner part of the tip section without removing the main component.

According to some embodiments, the multi-component cover comprises: a distal component configured to cover a distal part of the tip section; and a proximal component configured to cover a proximal part of the tip section, wherein the distal component and the proximal component are configured to abut to cover the tip section. According to some embodiments, the distal component may have a shape of a cylinder having a side wall and a front face, the front face is configured to cover a front part of the tip section and the proximal component has a shape of a cylinder having a side wall. According to some embodiments, the distal component may be configured for assembling over an inner part of the tip section from a distal part of the tip section and wherein the proximal component is configured for assembling over the inner part of the tip section from a proximal part of the tip section, such that the distal component and the proximal component are configured to join each other along a connection line, (which may be essentially perpendicular to the length of the tip section, for example, along an imaginary line extended between the two side cameras), such that the assembling does not cause damage to the a right/left side looking cameras or optical assemblies thereof.

The multi-component cover further comprises optical windows for one or more of: the front discrete illuminator, the right discrete illuminator, and the left discrete illuminator.

The multi-component cover may further comprise openings for one or more of: the front looking camera and/or an optical assembly thereof, the right side looking camera and/or an optical assembly thereof, and the left side looking camera and/or an optical assembly thereof.

The multi-component cover may further comprise a fluid channeling component adapted to channel fluid for insufflations and/or irrigation. The fluid channeling component may be a unitary component comprising a front fluid channel leading to a front opening at a distal end of the unitary fluid channeling component, for cleaning one or more front optical elements of the tip section, and a side fluid channel leading to a left side opening and to a right side opening in the unitary fluid channeling component, for cleaning side optical elements of the tip section. The unitary fluid channeling component further comprises a working channel adapted for the insertion of a medical tool. The unitary fluid channeling component further comprises a jet fluid channel adapted to clean a body cavity into which the endoscope is inserted.

According to some embodiments, the multi-component cover may further include openings for one or more of: a front I/I injector and/or a nozzle thereof, a side I/I injector and/or a nozzle thereof, a jet fluid channel, and a working channel.

According to some embodiments, the front looking camera, the front discrete illuminator, the right side looking camera, the right discrete illuminator, the left side looking camera, and the left discrete illuminator are configured to be installed on a single electronic circuit board.

According to some embodiments, the tip section has a diameter of about 17 mm or less. According to some embodiments, the tip section has a diameter of about 12 mm or less. According to some embodiments, the tip section has a diameter of about 10 mm or less. According to some embodiments, the tip section has a diameter of about 7 mm or less.

According to some embodiments, there is provided a method for assembling a multi-component cover on a tip section of a multi-camera endoscope, the method comprising: installing one or more optical windows on a first part of a multi-component cover; installing the first part of an inner part of a tip section; installing one or more optical windows on a second part of the multi-component cover; and installing the second part of the inner part of the tip section.

According to some embodiments, the first part of the multi-component cover comprises: a front-side component configured to cover a front part and a side part of the tip section; and the second part of the multi-component cover comprises: a side component configured to cover another side part of the tip section, wherein the front-side component and the side component are configured to abut to cover the tip section. The front-side component may be configured to cover the front part and a right side part of the tip section and the side component is configured to cover a left side part of the tip section. The front-side component may be configured to cover the front part and a left side part of the tip section and the side component is configured to cover a right side part of the tip section.

According to some embodiments, the first part of the multi-component cover comprises a front component configured to cover a front part; the second part of the multi component cover comprises a right side component configured to cover a right side part of the tip section; a third part of the multi component cover comprises a left side component configured to cover a left side part of the tip section; and the front, right side and left side components are configured to abut to cover the tip section.

According to some embodiments, the first part of the multi-component cover comprises a main component configured to cover the majority of the tip section and the second part of the multi-component cover comprises a removable window component configured to cover a window opening located on the main component, wherein the removable window component is configured to allow access to an inner part of the tip section without removing the main component.

According to some embodiments, the first part of the multi-component cover comprises a distal component configured to cover a distal part of the tip section and the second part of the multi-component cover comprises a proximal component configured to cover a proximal part of the tip section, wherein the distal component and the proximal component are configured to abut to cover the tip section. The distal component may have a shape of a cylinder having a side wall and a front face, the front face is configured to cover a front part of the tip section and the proximal component has a shape of a cylinder having a side wall.

According to some embodiments, there is provided a multi-component cover for the tip section of a multi-viewing element endoscope, said tip section comprising a front pointing viewing element and at least one side pointing viewing element, wherein each viewing element comprises an image sensor and a lens assembly, and each viewing element is associated with a discrete illuminator, said multi component cover comprising: a main component configured to cover the majority of said tip section; and a removable window component located on a side surface panel of said main component, said removable component configured to cover a window opening located on said main component, wherein said window opening is configured to allow access to an inner part of said tip section without removing said main component.

The window opening may be located on said side surface panel such that it aligns with said removable window component. The window opening may have edges that are adapted to couple to the removable window component.

The removable window component may comprise windows or openings for one or more of: said side pointing viewing element and/or an optical assembly thereof; a side discrete illuminator; and a side nozzle.

The multi-component cover may further comprise a removable window component positioned on a front end of said tip cover, said front removable component being configured to cover a front window opening which allows access to a front inner part of said tip section. The front removable window component may comprise openings for one or more of: said front pointing viewing element and/or an optical assembly thereof; a front discrete illuminator; a working/service channel; a front nozzle; and a front jet.

The cover may comprise more than one removable window component located on its side surfaces and each of said removable components may be configured to cover a window opening which allows access to an inner part of said tip section.

The main component may further include a groove on its side surface, said groove being configured to allow the removable window component to slide along the groove and be repositioned on, or removed from, the tip cover.

The removable window component may comprise a flat surface to assist in directing a cleaning fluid injected from an injector channel towards the side optical assembly and optical windows.

The tip section may have a diameter of 17 mm or less.

According to some embodiments, any one of the parts (components) of the multi-component cover may include a channel/cavity, for example, along one or more edges of the part (component), on an external and/or internal part of the part (component). The channel/cavity may be configured to contain one or more adhesives, such as glue, for connecting the parts (components) to each other and thus allowing better sealing of the tip cover.

According to some embodiments, there is provided herein an endoscope comprising the tip section as described herein. According to some embodiments, there is provided herein a colonoscope comprising the tip section as described herein.

According to some embodiments, there is provided herein a multi-camera endoscope, such as a colonoscope, comprising the tip section disclosed herein. According to some embodiments, the tip section of an endoscope (such as a colonoscope) is the most distal part of the endoscope which terminates the endoscope. The tip section is turnable by way of a bending section connected thereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 5B illustrates a front view of the multi-element tip cover of FIG. 5A in accordance with an embodiment of the present specification;

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

In the description and claims of the application, each of the words "comprise" "include" and "have", and forms thereof, are not necessarily limited to members in a list with which the words may be associated.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Figure 1A:
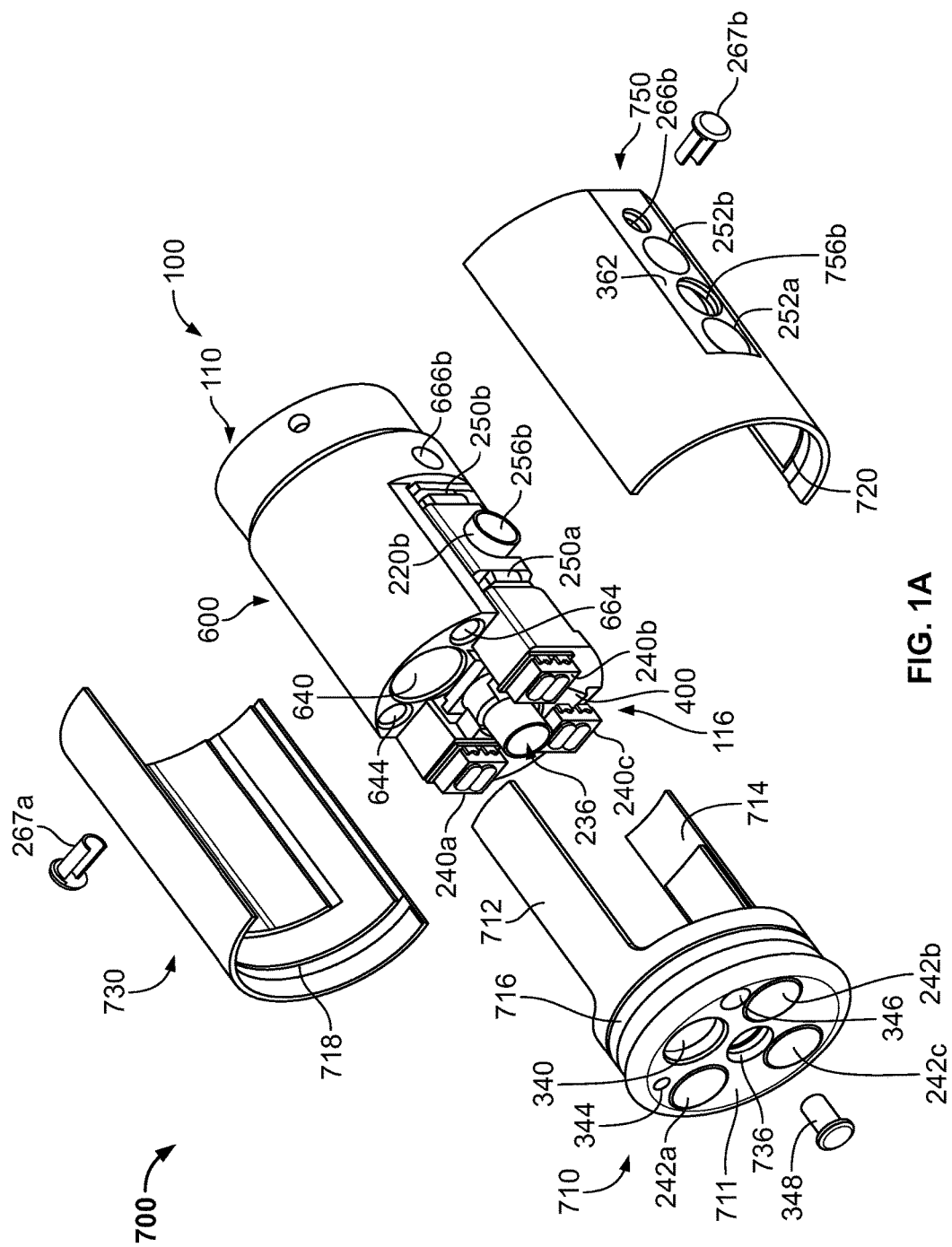
FIG. 1A schematically depicts an isometric view of a tip section of an endoscope (including an electronic circuit board carrying cameras and illumination sources, and fluid channeling component), having a multi-component tip cover (shown in an exploded view), according to an exemplary embodiment of the present specification.
Figure 1B:
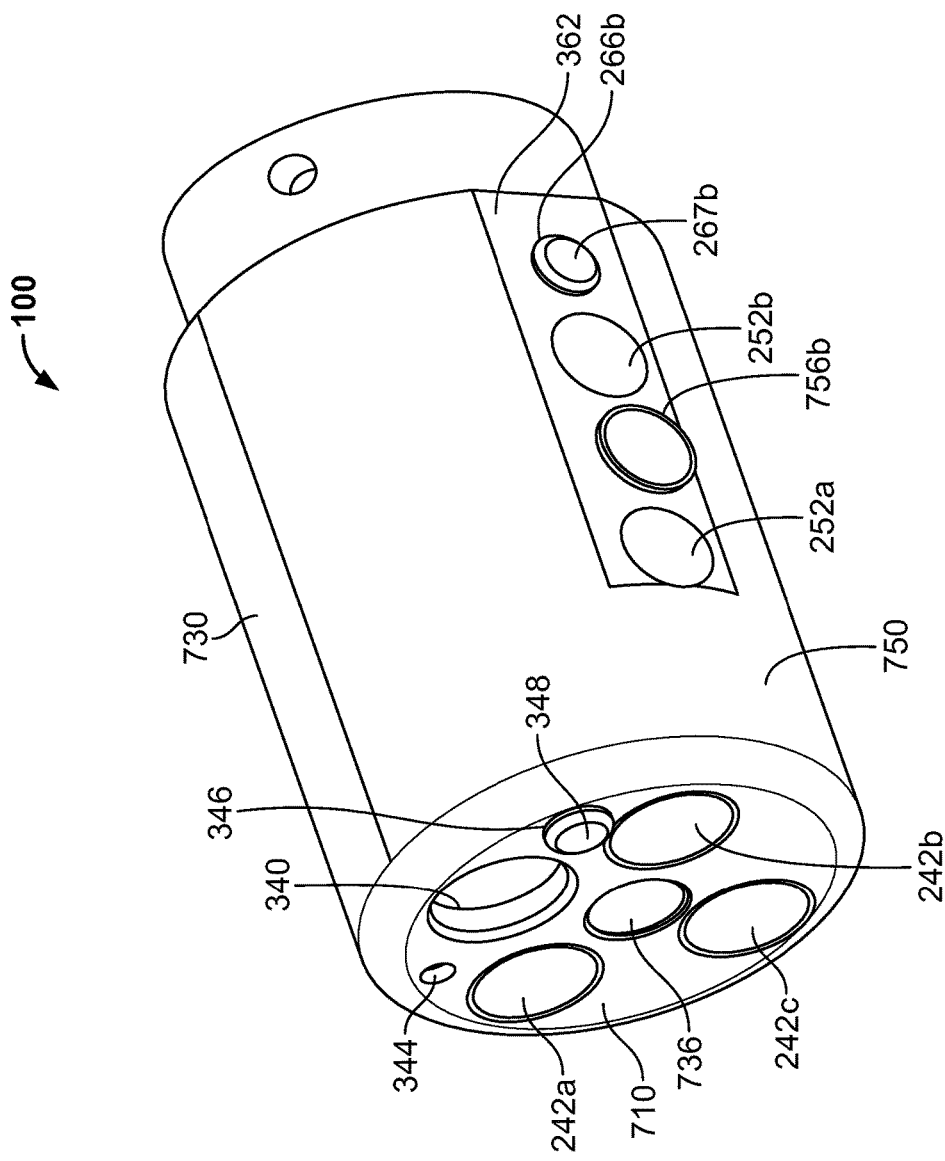
FIG. 1B schematically depicts an isometric view of the tip section of FIG. 1A, having an assembled multi-component tip cover, according to some exemplary embodiments of the present specification.

Reference is now made to FIG. 1A, which schematically depicts an isometric view of a tip section of an endoscope (including an electronic circuit board carrying cameras and illumination sources, and a fluid channeling component), having a multi-component tip cover (shown in an exploded view), according to an exemplary embodiment of the current specification and to FIG. 1B, which schematically depicts an isometric view of the tip section of FIG. 1A, having an assembled multi-component tip cover, according to some exemplary embodiments of the current specification.

Tip section 100 generally includes an inner part 110 which includes electronics (such as cameras, a circuit board such as electronic circuit board 400, and illumination sources, such as LEDs), fluid channels (such as fluid channeling component 600) and a multi-element tip cover 700. Multi-element tip cover 700 is designed to fit over the inner parts of the tip section 100, and to provide protection to the internal components in the inner part. Multi-element tip cover 700 includes, according to this embodiment, three parts: a front component 710 configured to cover a front part of the tip section; a right side component 730 configured to cover a right side part of the tip section; and a left side component 750 configured to cover a left side part of the tip section, wherein the front, right side and left side components are configured to abut each other to cover the tip section in such way that they cover essentially all inner parts of the tip section.

Front component 710 includes hole, transparent surface, window, or opening 736 configured to align with (and accommodate) front optical assembly 236 of forward looking camera 116; optical windows 242a, 242b and 242c of LEDs 240a, 240b and 240c; distal opening 340 of a working channel 640; distal opening 344 of a jet fluid channel 644; and irrigation and insufflation (I/I) injector 346 having a nozzle 348 (aligning with opening 664 of fluid channeling component 600).

Left side component 750 includes hole, transparent surface, window, or opening 756b configured to align with (and accommodate) side optical assembly 256b of side looking camera 220b; optical windows 252a and 252b of LEDs 250a and 250b on both sides of optical assembly 256b; side I/I injector 266b adapted to align with side I/I opening 666b of fluid component 600. Also seen in FIG. 1A and FIG. 1B are nozzles 267A and 267B for right side I/I injector (not shown) and left side I/I injector 266b respectively.

Right side component 730 includes similar elements (not shown) as left side component 750.

Left side component 750 and right side component 730 are each in a shape of essentially half a cylinder (without top and bottom).

Front component 710 has essentially a cup shape having two opposing arms 712 and 714 extending perpendicularly from the cup bottom 711 (which may also be referred to as the cup's front face) and protruding from the cup edges. Upon assembling of the tip cover components, front component 710 may be installed first, and then the side components 730, 750 such that their long edges meet each other on both sides over arms 712 and 714 to assure sealing (FIG. 1B). Adhesives, such as glue, may be added, for example, in cavities 716 (along the external parts of the edges of component 710), 718 (along the internal edges of component 730) and 720 (along the internal edges of component 750) to allow complete sealing of tip section 100.

Multi-element tip covers according to embodiments of the specification, such as multi-element tip cover 700 or any other multi-element tip cover as disclosed herein, solve a significant problem that exists in the art when attempts are made to pack all necessary components into the small inner volume of an endoscope tip and to cover and seal these components. Regular cup shaped tip covers are used for standard tips having just one front camera. However, when standard cup shaped tip covers are used to cover the multi-camera tip, protruding inner tip elements, such as lenses or other parts of the side optical assemblies, are often damaged during the sliding of the cover over them. Using a multi-element tip cover may solve this problem. In addition, a multi-element tip cover assists in aiming its holes/openings/windows exactly at their right place over the corresponding tip inner elements. This is almost impossible using a unitary piece cover. Moreover, separately sealing each one of the elements of the multi-element tip cover improves the overall sealing of the tip due to better access to each element (for example an optical window) compared to the limited access of the same element in a unitary piece cover, such as a cup shaped cover. Separately sealing (and optionally checking for satisfactory sealing) of each one of the elements of the multi-element tip cover may be performed prior to assembling of the cover. This may also improve the sealing of the tip.

According to an embodiment of the current specification, tip section 100 of an endoscope comprises at least a forwards looking camera and at least one side looking camera. Tip section 100 is turnable by way of a flexible shaft (not shown) which may also be referred to as a bending section (for example, a vertebra mechanism).

In some embodiments, the front-looking camera and/or any of the side-looking cameras comprises a Charge Coupled Device (CCD) or a Complementary Metal Oxide Semiconductor (CMOS) image sensor.

Tip section 100 includes front optical lens assembly 236 of forward looking camera 116. An optical axis of forwards looking camera 116 is substantially directed along the long dimension of the endoscope. However, since forward looking camera 116 is typically a wide angle camera, its Field Of View (FOV) may include viewing directions at large angles to its optical axis. It should be noted that the number of illumination sources, such as LEDs, used for illumination of the FOV may vary (for example, 1-5 LEDs may be used on a front face of tip section 100). Distal opening 340 of a working channel 640 is also located on the front face of tip section 100, such that a surgical tool inserted through working channel tube, and through the working channel 640 in the endoscope's tip section 100 and deployed beyond the front face may be viewed by forward looking camera 116.

Distal opening 344 of a jet fluid channel 644 is also located on the front face of tip section 100. In embodiments, distal opening 344 of a jet fluid channel 644 is be used for providing high pressure jet of fluid such as water or saline for cleaning the walls of the body cavity.

Also located on the front face of tip section 100 is an irrigation and insufflation (I/I) injector 346 having a nozzle 348 aimed at front lens optical assembly 236. In embodiments, I/I injector 346 is used for injecting fluid (liquid and/or gas) to wash contaminants such as blood, feces and other debris from front lens optical assembly 236 of forward looking camera 116. Optionally, the same injector is used for cleaning front lens optical assembly 236 and one, two or all of optical windows 242a, 242b and 242c. In embodiments, I/I injector 346 is fed by fluid such as water and/or gas which may be used for cleaning and/or inflating a body cavity.

Visible on a left side of tip section 100 is the side camera (side looking camera) element 256b of side looking camera 220b and optical windows 252a and 252b of LEDs 250a and 250b for camera 220b. A second side looking camera (not shown) is positioned on the right side of the tip and can be similar to camera 220b. Optical axis of the second side looking camera is substantially directed perpendicular to the long dimension of the endoscope. Optical axis of side looking camera 220b is substantially directed perpendicular to the long dimension of the endoscope. However, since side looking camera 220b and the second side looking camera are typically wide angle cameras, their fields of view may include viewing directions at large angles to their optical axes.

Side I/I injector 266b having a nozzle 267b aimed at side optical lens assembly 256b may be used for injecting fluid to wash contaminants such as blood, feces and other debris from side optical lens assembly 256b of side looking camera. In embodiments, the fluid includes gas which may be used for inflating a body cavity. Optionally, the same injector is used for cleaning both side optical lens assembly 256b and optical windows 252a and/or 252b. It is noted that according to some embodiments, the tip includes more than one window and LEDs, on the side and more than one window and LEDs in the front (for example, 1-5 windows and two LEDs on the side). Similar configuration of I/I injector and nozzle (not shown) exists for cleaning the optical lens assembly and optical windows (not shown) located on the other side of tip 100. The I/I injectors are configured to clean all or a part of these windows/LEDs. In various embodiments, left side I/I injector 266b, right side I/I injector (not shown), and front side I/I injector 344 are fed from the same channel in the fluid channeling component 600. In other embodiments, front side I/I injector is 344 is fed from a first fluid channel and left side I/I injector 266b and right side I/I injector are fed from a second, separate fluid channel in the fluid channeling component 600.

It is noted that the right side wall (not shown) and left side wall 362 have a form of an essentially flat surface which assists in directing the cleaning fluid injected from the right side I/I injector (not shown) and the left side injector 266b towards the right side optical assembly and windows and the left side optical assembly 256b and optical windows 252a and/or 252b respectively. Lack of such a flat surface may result in dripping of the cleaning fluid along the curved surface of tip section 100 of the endoscope without performing the desired cleaning action.

It should be noted that while only one side looking camera can be seen in FIG. 1A and FIG. 1B, preferably at least two side looking cameras are located within tip section 100. When two side looking cameras are used, the side looking cameras are preferably installed such that their field of views are substantially opposing. However, different configurations and number of side looking cameras are possible within the general scope of the current specification.

According to some embodiments, the circuit board used for carrying electronic components, such as cameras and/or LEDs, is a flexible circuit board that consumes less space and leaves more volume for additional necessary features. The flexibility of the board adds another dimension in space that can be used for components positioning.

The use of a flexible circuit board, according to embodiments of the specification, significantly increases reliability of the electric modules connection thereto as no wires are required for components connectivity. In addition, according to some embodiments, the components assembly can be machined and automatic.

The use of a flexible circuit board, according to some embodiments of the specification, also allows components (parts) movement and maneuverability during assembly of the camera head (tip of the endoscope) while maintaining a high level of reliability. The use of the circuit board, according to some embodiments of the specification, also simplifies the (tip) assembling process.

According to some embodiments, a flexible circuit board is connected to the control unit via a multi-wire cable. This cable is welded on the board in a designated location, freeing additional space within the tip assembly and adding flexibility to cable access. Assembling the multi-wire cable directly to the electrical components presents a major challenge which is mitigated by the use of the flexible board according to embodiments of the specification.

Figure 2:
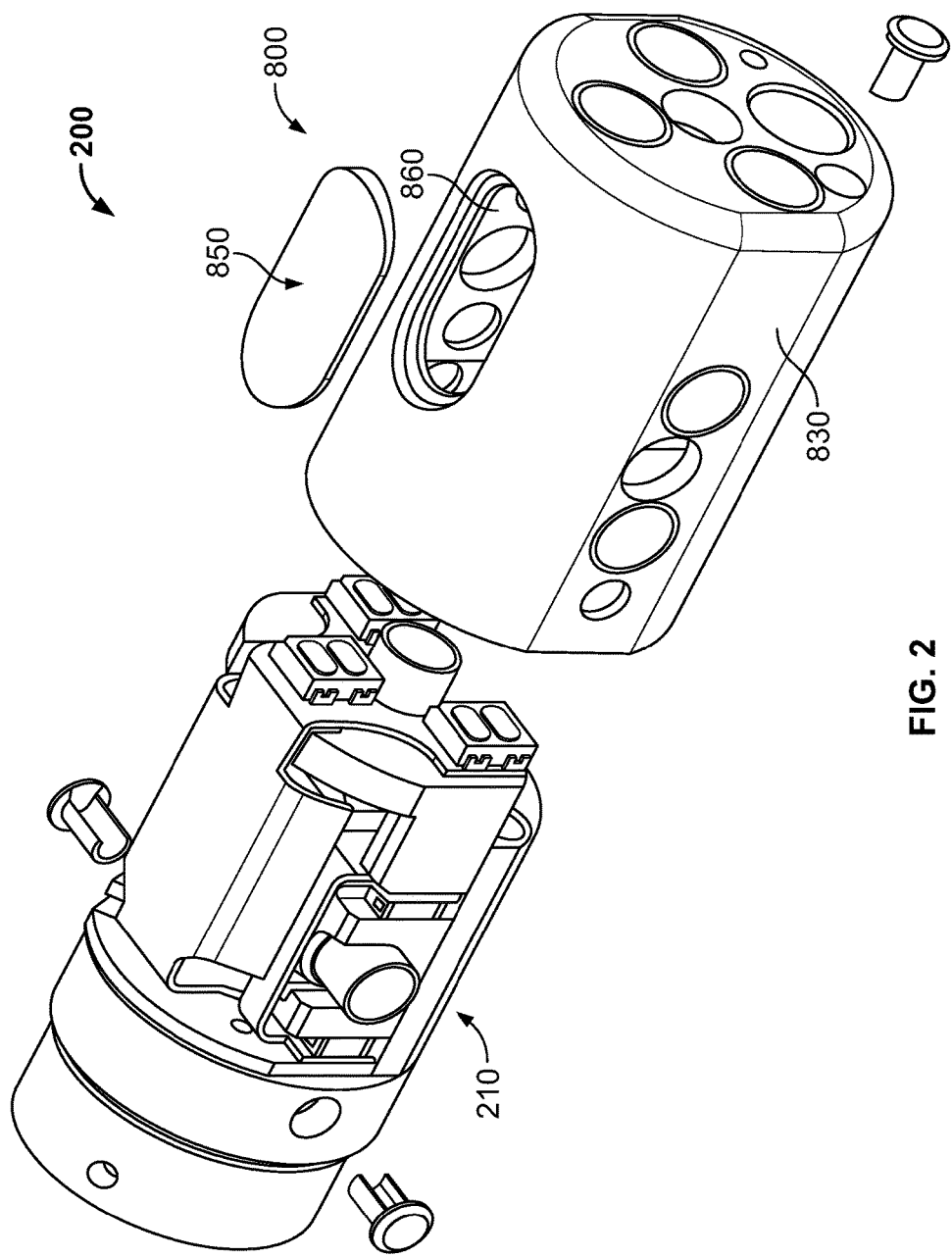
FIG. 2 schematically depicts an isometric view of a tip section of an endoscope (including an electronic circuit board carrying cameras and illumination sources, and a fluid channeling component), having a multi-component tip cover (shown in an exploded view), according to another exemplary embodiment of the present specification.

Reference is now made to FIG. 2, which schematically depicts an isometric view of a tip section of an endoscope (including an electronic circuit board carrying cameras and illumination sources, and a fluid channeling component), having a multi-component tip cover (shown in an exploded view), according to an exemplary embodiment of the current specification. Tip section 200 generally includes an inner part 210 which may be similar to inner part 110 of tip section 100 of FIGS. 1A-1B and a multi-element tip cover 800. Multi-element tip cover 800 is designed to fit over the inner part 210 of the tip section 200, and to provide protection to the internal components in the inner part 210. Multi-element tip cover 800 includes, according to this embodiment, a main component 830 configured to cover the majority of the tip section, and a removable window component 850 configured to cover a window opening 860 located on main component 830, such that removable window component 850 is configured to allow access to an inner part 210 of tip section 200 without removing main component 830. This allows fixing or replacing one of the components of inner part 210 (such as a LED, an optical element or any other element) without removing main component 830 and damaging the packing and sealing of tip section 200.

Main component 830 has essentially a cup shape having a front face part configured to cover the front face of tip section 200 and cup edges configured to cover the side surface of tip section 200.

Main component 830 may further includes front and side holes, openings, windows and surfaces similar to those of multi-component cover 700 of FIG. 1A and FIG. 1B.

Figure 3:
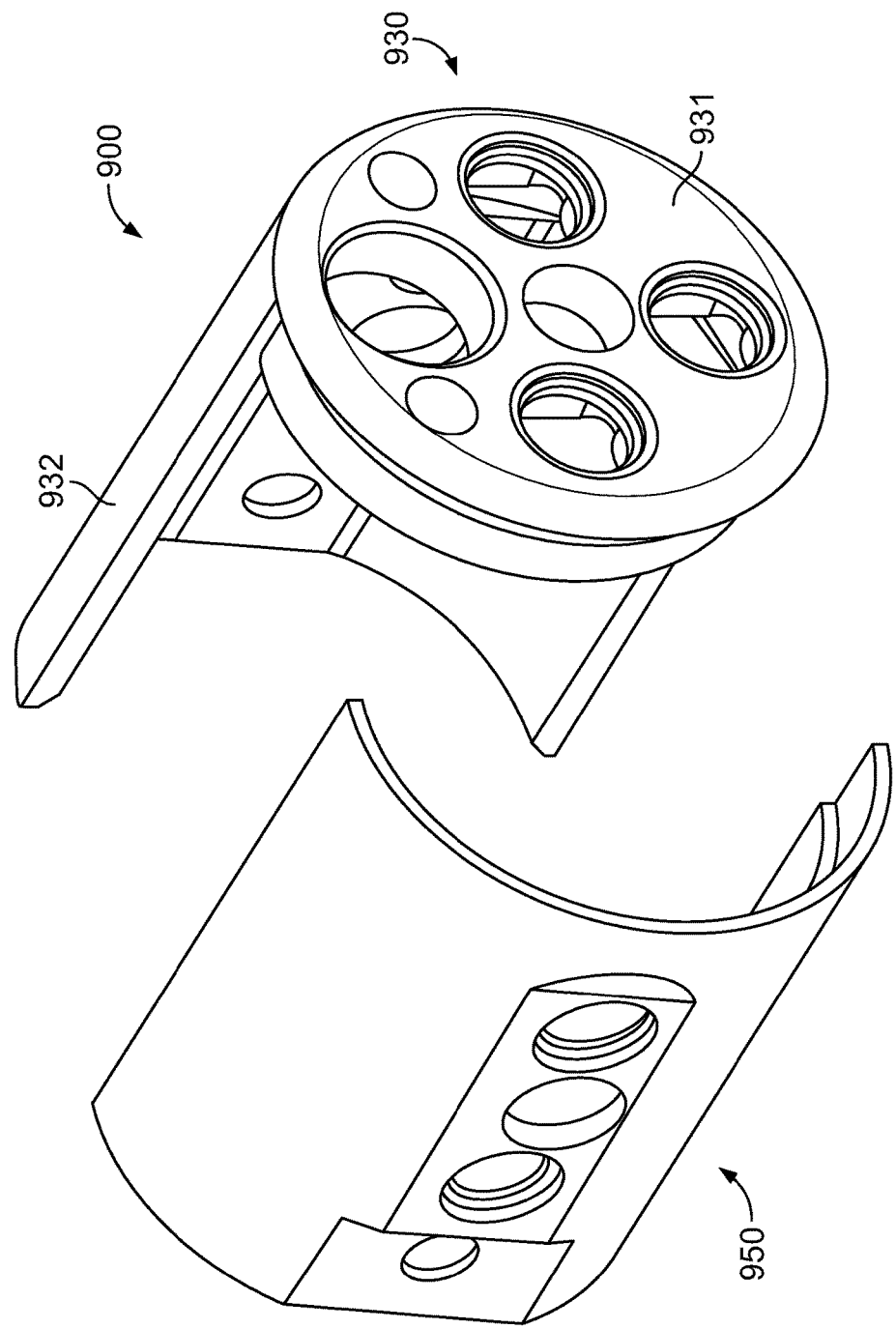
FIG. 3 schematically depicts an exploded view of a multi-component tip cover, according to an exemplary embodiment of the present specification.

Reference is now made to FIG. 3, which schematically depicts an exploded view of a multi-component tip cover, according to an exemplary embodiment of the current specification. Multi-element tip cover 900 is designed to fit over the inner part (not shown) of a tip section and to provide protection to the internal components in the inner part. Multi-element tip cover 900 includes, according to this embodiment, a front-side component 930, comprising a front portion 931 and a side portion 932, configured to cover a front part and a side part of the tip section, and a side component 950 configured to cover another side part of the tip section, wherein front-side component 930 and side component 950 are configured to abut to cover the tip section.

Figure 4A:
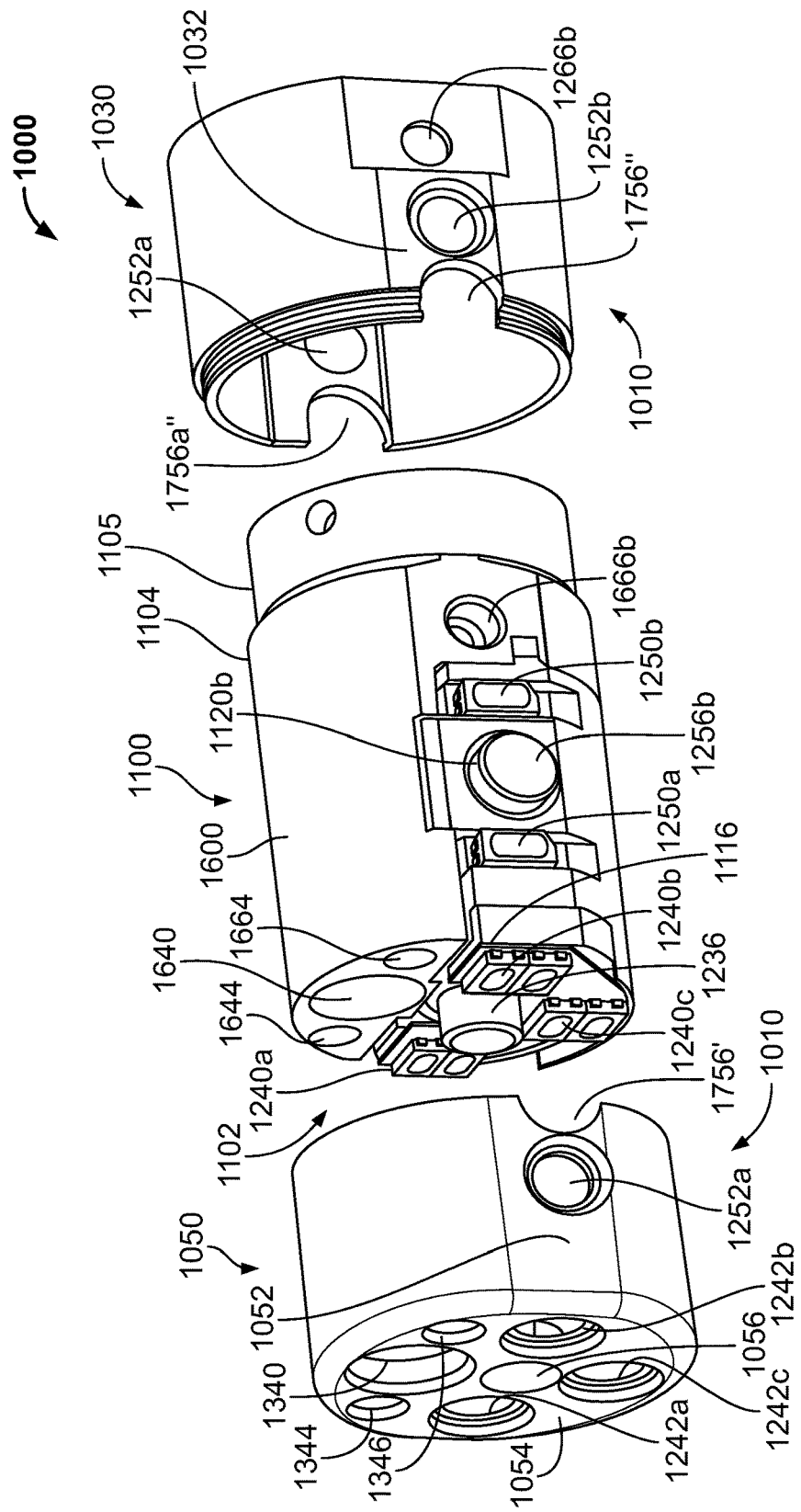
FIG. 4A schematically depicts an isometric view of a tip section of an endoscope (including an electronic circuit board carrying cameras and illumination sources, and a fluid channeling component), having a multi-component tip cover (shown in an exploded view), according to another exemplary embodiment of the present specification.
Figure 4B:
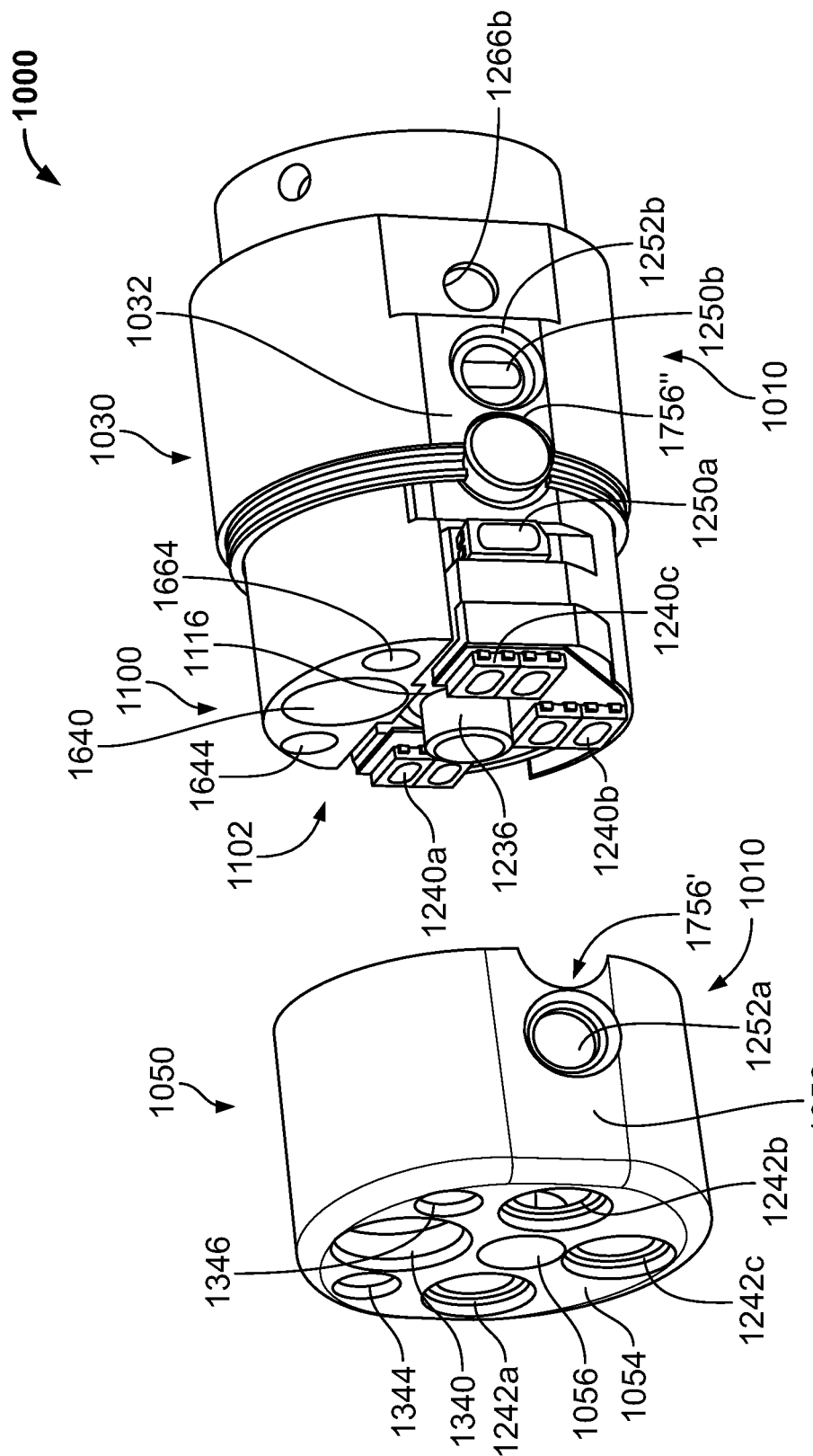
FIG. 4B schematically depicts an isometric view of the tip section of FIG. 4A, having a multi-component tip cover (partially in an exploded view), according to an exemplary embodiment of the present specification.
Figure 4C:
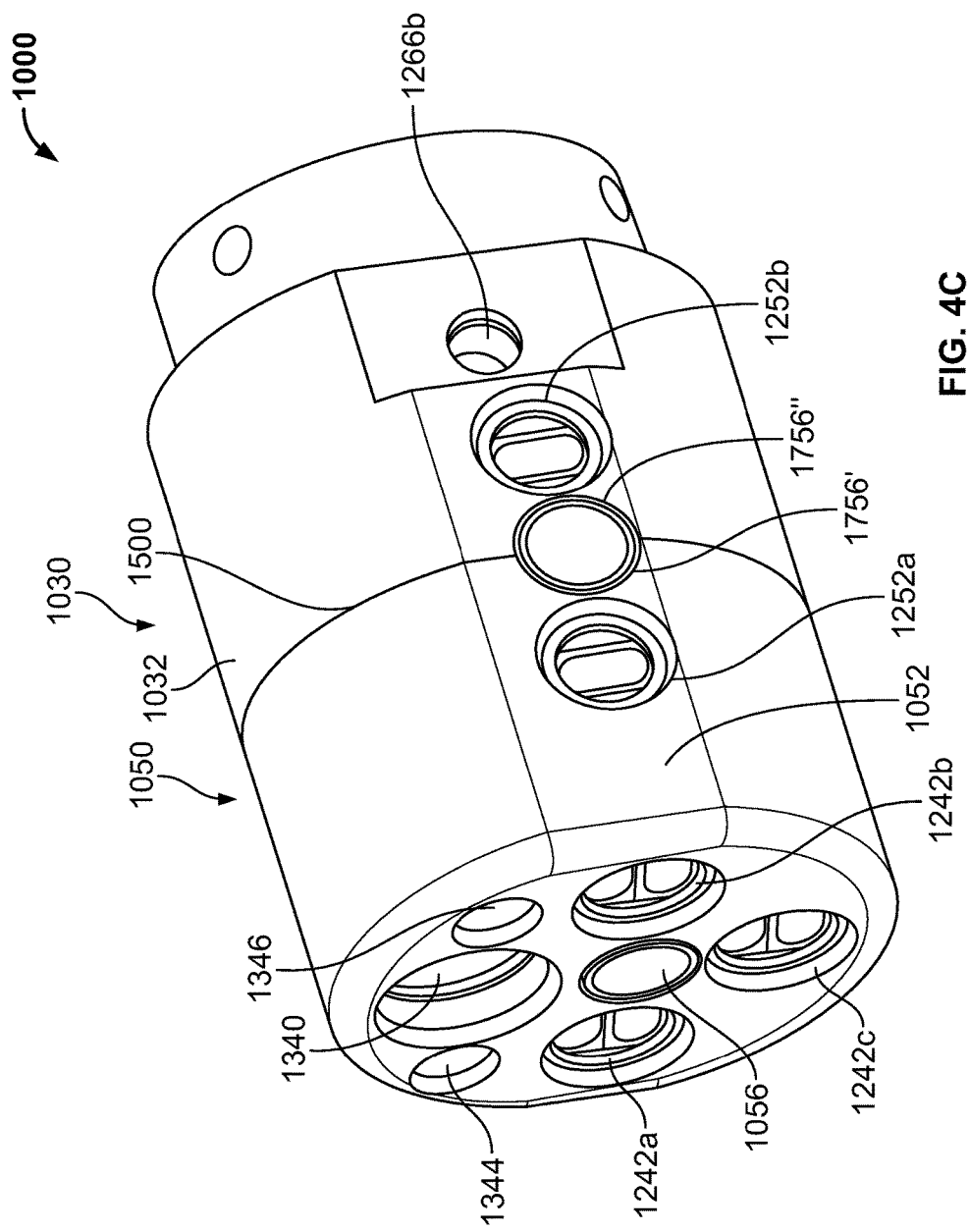
FIG. 4C schematically depicts an isometric view of the tip section of FIG. 4A having an assembled multi-component tip cover, according to an exemplary embodiment of the present specification.

Reference is now made to FIGS. 4A through 4C. FIG. 4A schematically depicts an isometric view of a tip section of an endoscope (including an electronic circuit board carrying cameras and illumination sources, an electronic circuit board holder, and a fluid channeling component), having a multi-component tip cover (shown in an exploded view), according to an exemplary embodiment of the current specification. FIG. 4B schematically depicts an isometric view of the tip section of FIG. 4A, having a multi-component tip cover (partially in an exploded view), according to an exemplary embodiment of the current specification. FIG. 4C schematically depicts an isometric view of the tip section of FIG. 4A having an assembled multi-component tip cover, according to an exemplary embodiment of the current specification.

Tip section 1000 generally includes an inner part 1100 which includes electronics (such as cameras, a circuit board, and LEDs), fluid channels (such as fluid channeling component 1600) and a multi-element tip cover 1010. Multi-element tip cover 1010 is designed to fit over the inner parts of the tip section 1000 and to provide protection to the internal components in the inner part 1100. In various embodiments, the tip section 1000 comprises three parts/portions: a distal/front part 1102, a proximal part 1104 and a rear part 1105. Multi-element tip cover 1010 includes, according to this embodiment, two parts: a distal component 1050 configured to cover a distal/front part 1102 of the tip section and a proximal component 1030 configured to cover a proximal part 1104 of the tip section, wherein the distal component and the proximal component are configured to abut to cover the tip section 1000. Distal component 1050 has a shape of a cylinder having a side wall 1052 and a front face 1054, wherein front face 1054 is configured to cover a front part 1102 of inner part 1100 of tip section 1000 and proximal component 1030 has a shape of a cylinder having a side wall 1032 without a top or a bottom configured to cover a proximal part 1104 of inner part 1100 of tip section 1000. In accordance with an embodiment, the proximal component 1030 of the tip cover 1010 does not cover a rear part 1105 of the tip section 1000, but only the proximal part 1104. This enables connection between a bending section of the endoscope and the tip section 1000 to be on the rear part 1105 thereby effectively reducing the non-flexible portion of the bending section.

Distal component 1050 includes on front face 1054 thereof hole, transparent surface, window or opening 1056 configured to align with front optical assembly 1236 of forwards looking camera 1116; optical windows 1242a, 1242b and 1242c of LEDs 1240a, 1240b and 1240c; distal opening 1340 of a working channel 1640; distal opening 1344 of a jet fluid channel 1644; and I/I injector 1346 (aligning with opening 1664 of fluid channeling component 1600).

Distal component 1050 further includes on side wall 1052 thereof optical windows 1252a of LED 1250a and on an opposing side of side wall 1052 another optical window of another LED (not shown).

Distal component 1050 further includes on the edge of side wall 1052 thereof a recess 1756' (essentially in a shape of half a hole) configured to accommodate (along with a recess 1756" on the edge of side wall 1032 of proximal component 1030) optical assembly 1256b of side looking camera 1120b. On an opposing side of side wall 1052 there may be a similar recess (not shown) to accommodate (along with another recess on the edge of an opposing side of side wall 1032 of proximal component 1030) an optical assembly (not shown) of a side looking camera (not shown) located on the other side of inner part 1100. Proximal component 1030 includes on side wall 1032 thereof optical windows 1252b of LED 1250b and on an opposing side of side wall 1032 another optical window 1252a of another LED (not shown).

Proximal component 1030 further includes on the edge of side wall 1032 thereof a recess 1756" (essentially in a shape of half a hole) configured to accommodate (along with recess 1756' on the edge of side wall 1052 of distal component 1050) optical lens assembly 1256b of side looking camera 1120b. On an opposing side of side wall 1032 there is a similar recess 1756a" to accommodate (along with another recess on the edge of an opposing side of side wall 1152 of proximal component 1050) an optical assembly (not shown) of a side looking camera (not shown) located on the other side of inner part 1100.

Proximal component 1030 further includes side I/I injector 1266b adapted to align with side I/I opening 1666b.

Other parts of inner part 1100 of tip section 1000 may generally be similar to inner part 1100 of tip section 100 of FIGS. 1A, 1B. The method of assembling tip section 1000 over inner part 1100 may include assembling distal component 1050 from the distal/front part 1102 of tip section 1000, assembling proximal component 1030 from the proximal part 1104 of tip section 1000 and joining distal component 1050 and proximal component 1030 along their edges (line 1500) such that none of the tip cover components slides over the optical assemblies of the side looking cameras.

In yet another embodiment, the present specification discloses a multi-element tip cover that not only provides protection to the internal components of the endoscope tip, but also facilitates easy access to the internal components in the tip section, such that a component may be removed or replaced if required without having to remove the tip cover.

The present embodiments disclose a novel assembly approach of the tip cover on the distal tip and also provide a novel solution to the problem of replacing broken outer windows of the camera and illuminators. Additionally, efficient solutions are provided for replacing internal components of the distal tip, such as sensors, cables, illuminators, internal lenses, and other such components.

As shown earlier with reference to FIG. 4A, tip section 1000 generally includes an inner part 1100 which includes an electronic circuit board that carries cameras and illumination sources, and a fluid channeling component 1600.

In an embodiment, a multi-element tip cover is designed to fit over the inner part 1100 of the tip section 1000 and to provide protection to the internal components in the inner part 1100.

Figure 5A:
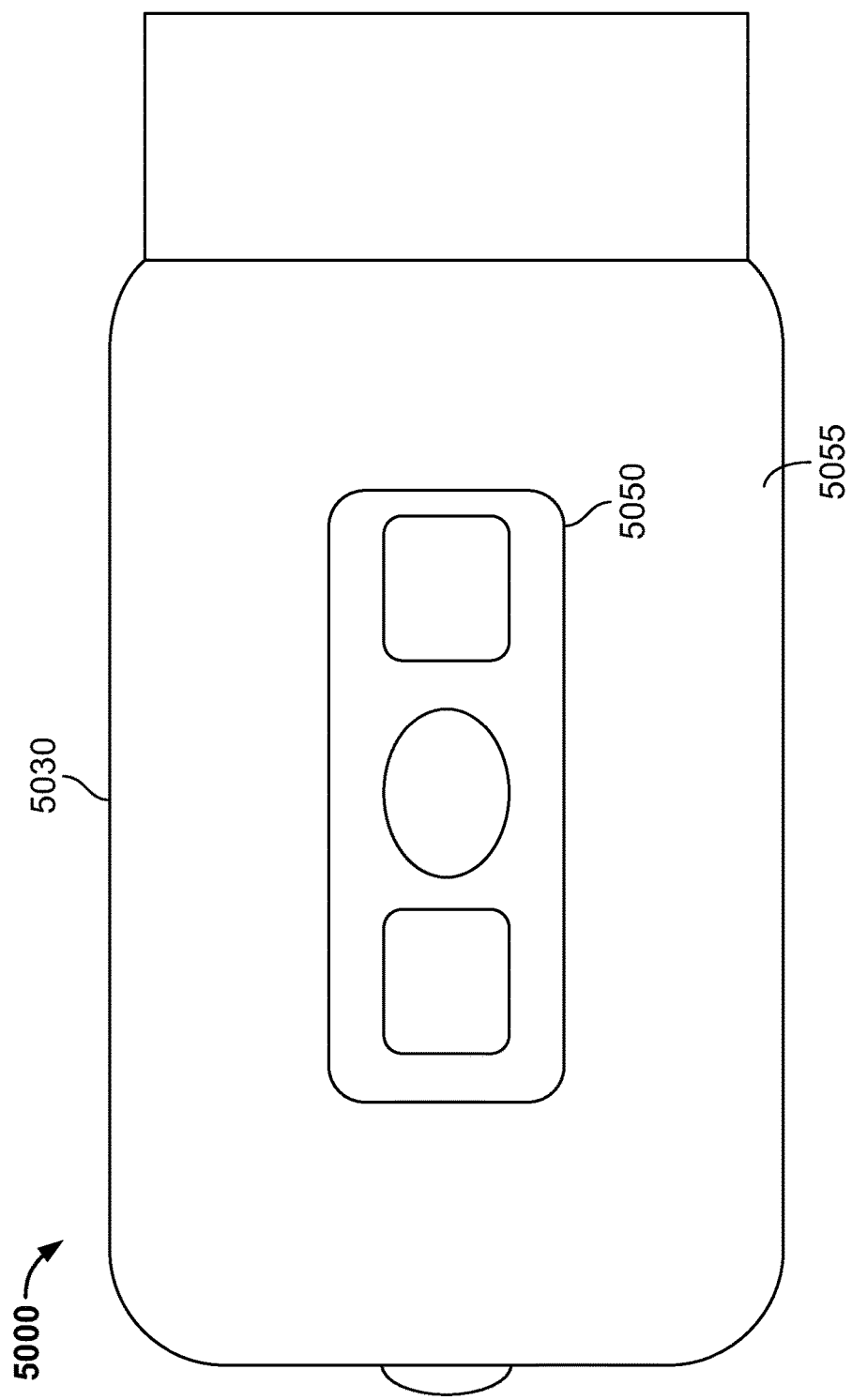
FIG. 5A illustrates a side view of a multi-element tip cover in accordance with an embodiment of the present specification.

FIG. 5A and FIG. 5B illustrate side and front views respectively of a multi-element tip cover 5000 in accordance with an embodiment of the present specification. In an embodiment, the multi-element tip cover includes a main component portion 5030. The main component 5030 of the tip cover is substantially cylindrical in an embodiment, and is configured to cover a major portion of the tip section of an endoscope. As known in the art, the diameter of the distal tip of an endoscope varies from scope to scope. Therefore, in an embodiment, the size of the tip cover is customized such that it fits the dimensions of the corresponding distal tip. In various embodiments, the diameter of the main component 5030 of the tip cover 5000 varies from 2 to 17 millimeters. In an embodiment, the tip cover 5000 is made up of suitable materials known in the art such as PEEK (polyether ether ketone), or other polymer based materials. In an embodiment, the main component 5030 of the tip cover 5000 further comprises a removable window component (a side removable panel) 5050, located on a side surface wall 5055. The window component 5050 is configured to cover a window opening (not shown) located on main component 5030. In an embodiment, the window opening is designed to provide access to the inner part of the tip section which includes components such as viewing elements and associated optics and lenses, illuminators, sensors, and other components located inside.

Thus, the removable window component 5050 is designed such that it can be removed to gain access to the window opening, through which the internal components of the tip can be accessed for repair or replacement, without removing the main component 5030. Therefore, for fixing or replacing one or more components of the inner part of the tip section, such as an LED, an optical element or any other element, the entire tip is not opened or exposed. Further, the main component 5030 of the tip cover remains intact and protects the packing and sealing of the tip section from damage. In various embodiments, the removable window component 5050 comprises a surface area in a range of 30 to 85% of the total surface area of the cylindrical side wall 5055 of the tip cover 5000. In various embodiments, an aspect ratio of width to length of the removable window component 5050 is in a range of 1:6. In various embodiments, when the removable window component 5050 is in place on said main component 5030, the windows of the removable window component 5050 and the underlying optical elements and/or LEDs are aligned such that a distance from the windows of the removable window component 5050 to the underlying optical elements and/or LEDs is in a range of 0 to 3 millimeters, and any increment therein, preferably 0 to 1 millimeters.

In an embodiment, the multi-element tip cover comprises three window openings with removable window components—one on the front for accessing front viewing element and other components located in the front section of the distal tip and one each on the two sides for accessing the corresponding side viewing elements and other components located on the two sides of the distal tip. The front removable window component comprises a surface area in a range of 20 to 85% of the total surface area of the front distal surface of the tip cover and the side window components each comprise a surface area in a range of 30 to 85% of the total surface area of the cylindrical side wall of the tip cover. In various embodiments, the front removable window component has any one of a circular, oval (as described with reference to FIG. 7 below), square, rectangular, or irregular shape. An aspect ratio of width to length of the front window component is in a range of 1:6 and an aspect ratio of width to length of each side removable window component is in a range of 1 to 6. When the front removable window component and side removable window components are in place, the windows or openings of the front removable window component and the underlying optical elements and/or LEDs are aligned such that a distance from the windows or openings of the front removable window component to the underlying optical elements and/or LEDs is in a range of 0 to 3 millimeters, and any increment therein, and the windows or openings of the side removable window components and the underlying optical elements and/or LEDs are aligned such that a distance from the windows or openings of each side removable window component to the underlying optical elements and/or LEDs is in a range of 0 to 3 millimeters, and any increment therein.

In another embodiment (shown in FIGS. 6A, 6B and 8), the multi-element tip cover comprises only side window openings with side removable window components. The side removable window components each comprise a surface area in a range of 30 to 85% of the total surface area of the cylindrical side wall of the tip cover. An aspect ratio of width to length of each side removable window component is in a range of 1:6. When the side removable window components are in place, the windows or openings of the side removable window components and the underlying optical elements and/or LEDs are aligned such that distance from the windows or openings of each side removable window component to the underlying optical elements and/or LEDs is in a range of 0 to 3 millimeters, and any increment therein.

In yet another embodiment, the multi-element tip cover comprises a front window opening with removable front window component and only one side window opening with removable side window component. The front window opening component comprises a surface area in a range of 20 to 85% of the total surface area of the front distal surface of the tip cover and the side window component comprises a surface area in a range of 30 to 85% of the total surface area of the cylindrical side wall of the tip cover. An aspect ratio of width to length of the front window component is in a range of 1:6 and an aspect ratio of width to length of the side removable window component is in a range of 1:6. When the front removable window component and side removable window component are in place, the windows or openings of the front removable window component and the underlying optical elements and/or LEDs are aligned such that a distance from the windows or openings of the front removable window component to the underlying optical elements and/or LEDs is in a range of 0 to 3 millimeters, and any increment therein, and the windows or openings of the side removable window component and the underlying optical elements and/or LEDs are aligned such that a distance from the windows or openings of the side removable window component to the underlying optical elements and/or LEDs is in a range of 0 to 3 millimeters, and any increment therein.

Referring to FIG. 5B, a front view of the multi-element tip cover 5000 is shown, in accordance with an embodiment of the present specification. The figure shows a front face part (front panel) 5080 of the main component 5030 of the tip cover 5000, and is configured to cover the front face of the tip section. In an embodiment, front face part 5080 further includes openings and windows to correspond to front panel of the tip section, as shown earlier with respect to FIG. 4A.

Thus, the front face part 5080 includes windows 5240a, 5240b, and 5240c for the illuminators of the front viewing element and window 5236 for the front viewing element camera (image sensor) located in the front portion of the tip section. In various embodiments, central window 5236 is aligned with the front viewing element such that the underlying front viewing element is within a range of 0 to 3 millimeters, and any increment therein, from central window 5236. Window 5240a is located at a position corresponding to 9 o'clock relative to central window 5236 and is within a range of 0 to 3 millimeters, and any increment therein, from an underlying illuminator. Window 5240b is located at a position corresponding to 3 o'clock relative to central window 5236 and is within a range of 0 to 3 millimeters, and any increment therein, from an underlying illuminator. Window 5240c is located at a position corresponding to 6 o'clock relative to central window 5236 and is within a range of 0 to 3 millimeters, and any increment therein, from an underlying illuminator.

In other embodiments, the front face 5080 of the tip cover 5000 further includes a distal opening of a working channel, distal opening of a jet fluid channel, and I/I injector aligning with an opening of a fluid channeling component. For the purpose of clarity and simplicity, these openings are not shown in FIG. 5B.

Figure 5C:
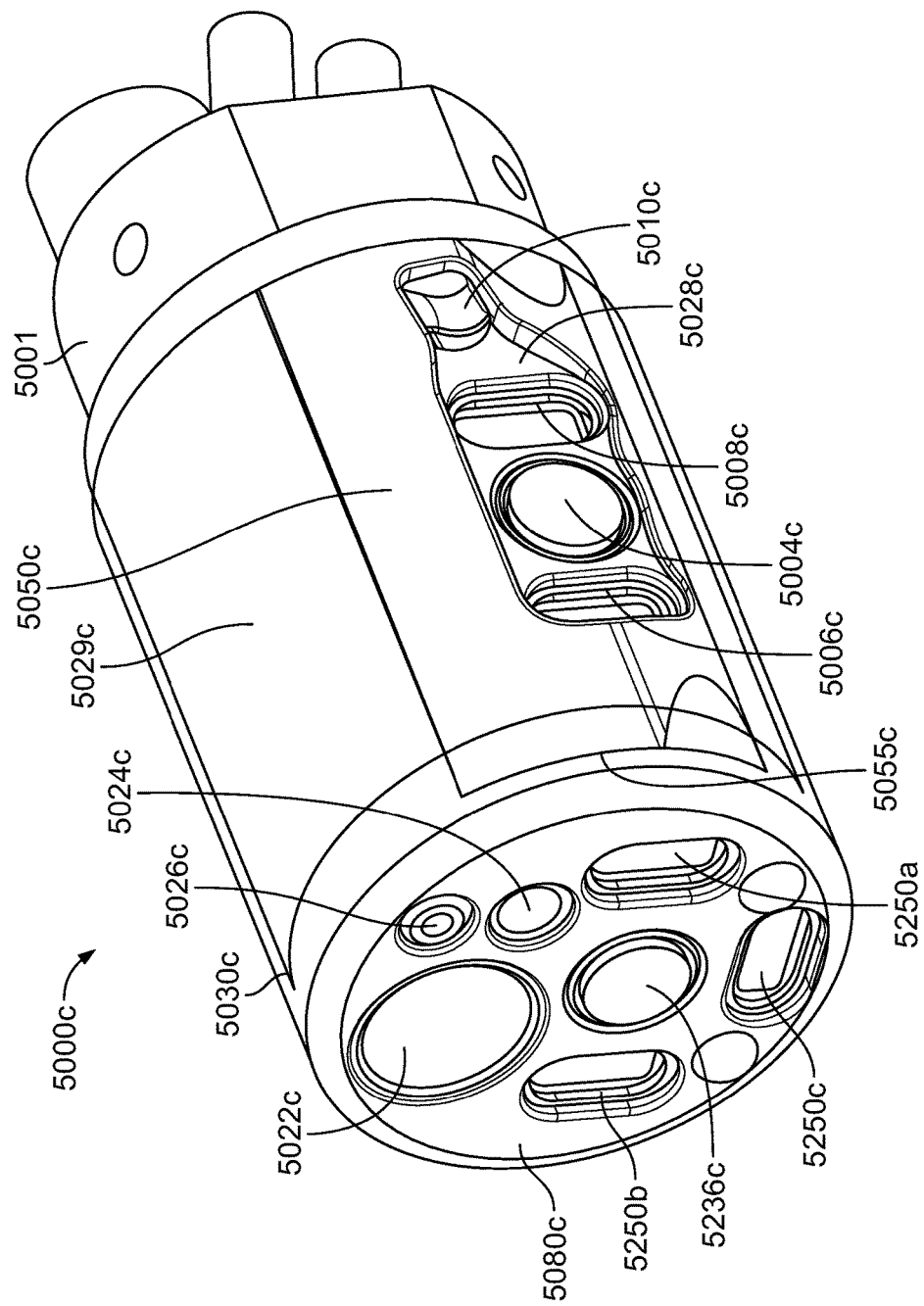
FIG. 5C illustrates an isometric view of a multi-element tip cover positioned over the inner parts of a tip section of a multiple viewing elements endoscope, in accordance with an embodiment of the present specification.

FIG. 5C shows an isometric view of another embodiment of a multi-element tip cover 5000c. Referring to FIG. 5C, the multi-element tip cover 5000c has a main component portion 5030c and a side removable window component 5050c located in a side panel recess or opening 5055c of the main component portion 5030c. The side removable window component 5050c is sized and configured to fit within side panel opening or recess 5055c. Main component portion 5030c is configured to cover a major portion of a tip section 5001 of an endoscope. The side removable window component 5050c, in an embodiment, is in the form of a removable panel. In an embodiment, the side removable window component 5050c comprises a flat depression 5028c which comprises a window or opening 5004c for a side optical lens assembly, optical windows 5006c, 5008c for illuminators, and a side nozzle opening 5010c for a side nozzle.

A front panel 5080c is positioned on a front end of the tip cover 5000c. The front panel 5080c comprises a window or opening 5236c for a front optical lens assembly, optical windows 5250a, 5250b and 5250c for front illuminators, a working/service channel opening 5022c, a nozzle opening 5024c and a jet opening 5026c.

It may be noted that the overall shape of the distal tip is substantially round, yet the side components including the side camera, LEDs, and jet are placed in flat depression 5028c. This flat depression 5028c is located on a surface of the side removable window component 5050c.

In an embodiment, multi-element tip cover 5000c has one side removable window component 5050c on one side. In another embodiment, multi-element tip cover 5000c has more than one side removable window component on its tip side surfaces to enable easy access to the internal components in the tip section, such that a component may be removed or replaced if required without having to remove the entire tip cover 5000c.

Figure 5D:
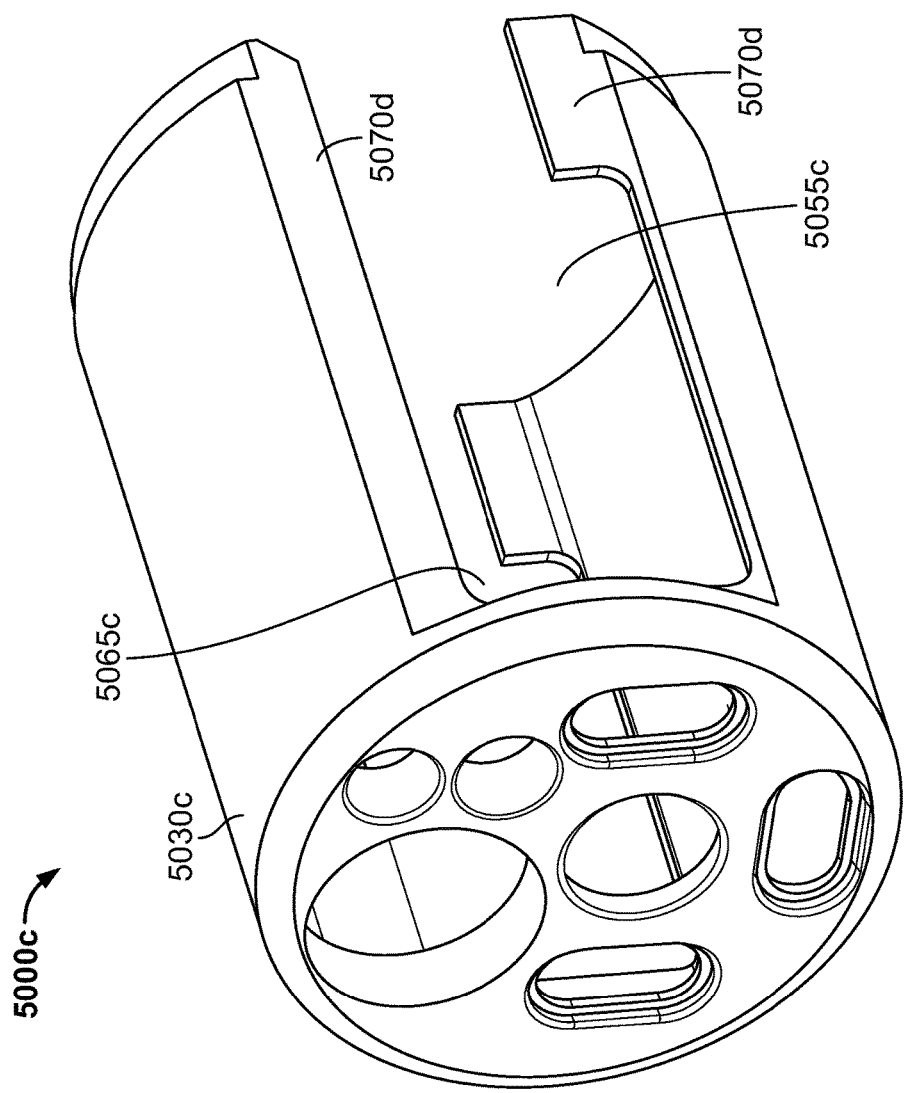
FIG. 5D is an isometric view of a main component portion of the multi-element tip cover of FIG. 5C in accordance with an embodiment of the present specification.

FIG. 5D shows another isometric view of the multi-element tip cover 5000c of FIG. 5C. In this figure, the side removable window component (shown as side removable window component 5050c in FIG. 5C) is removed, exposing side panel opening or recess 5055c. In an embodiment, the side panel opening or recess 5055c is positioned on the circumference of the endoscope tip at a distance (depth) ranging from approximately 1 to 9 millimeters from the surface of the tip, and in an embodiment is positioned at approximately 7.0 or 7.9 millimeters, from the surface of the tip.

In an embodiment, the main component portion 5030c comprises edges 5070d about the side panel opening or recess 5055c that are adapted to couple to the side removable window component, in a manner such that the side removable window component may easily be put on to cover the side panel opening or recess 5055c and may also be easily removed. In an embodiment, the side removable window component may be coupled to the edges 5070d of the main component portion 5030c by any suitable coupling means known in the art, such as but not limited to screws, hinges, hooks, adhesives or welding. Optionally, in some embodiments, wherein an endoscope includes side viewing elements on both sides of a tip section, the tip cover 5000c includes another side panel opening or recess 5065c positioned on the opposite side of side panel opening or recess 5055c and another side removable window component similar to the side window component 5050c for side panel opening or recess 5065c.

Figure 5E:
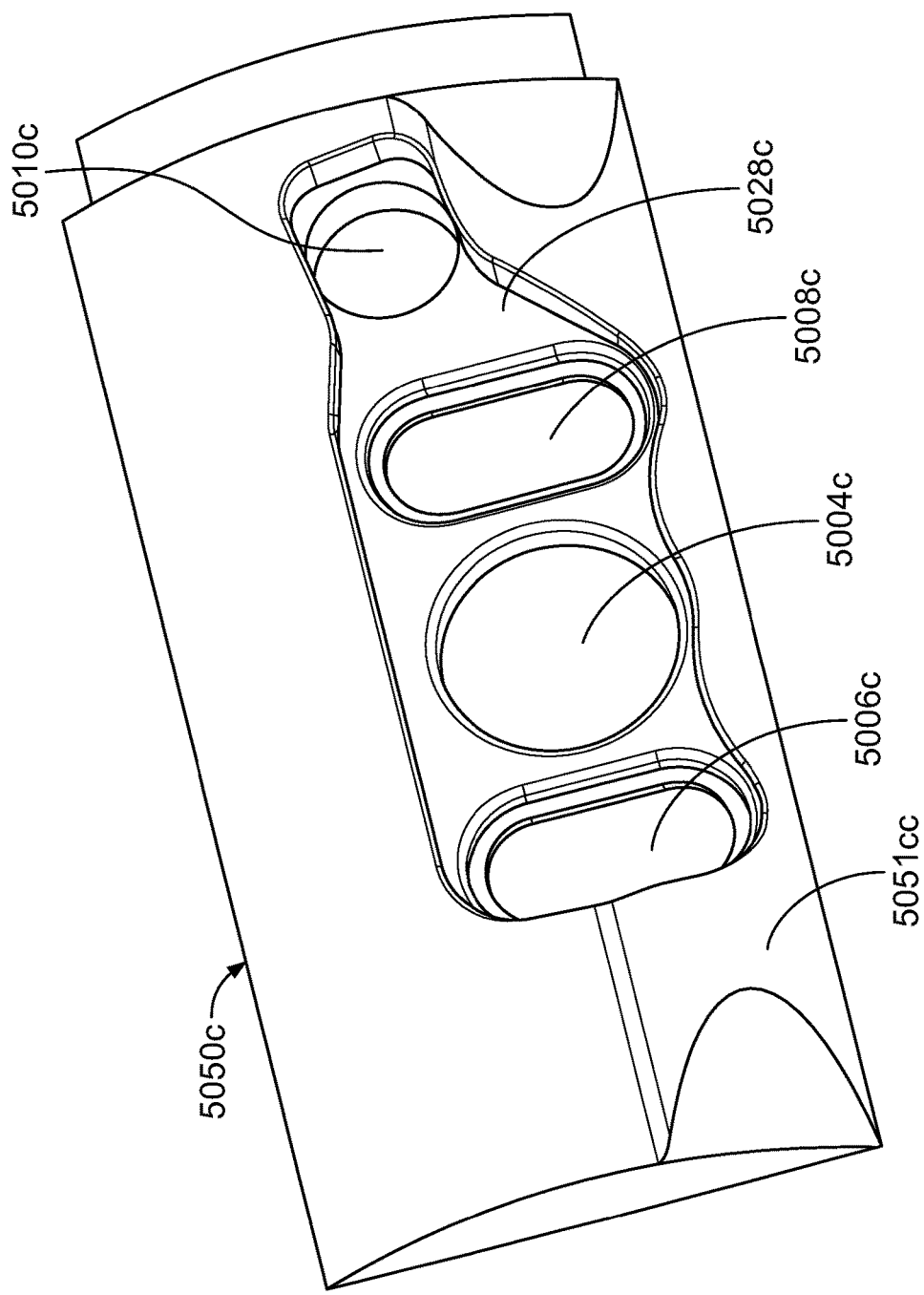
FIG. 5E is an isometric view of a removable window component of the multi-element tip cover of FIG. 5C, according to an embodiment of the present specification.

FIG. 5E shows the side removable window component 5050c for the multi-element tip cover 5000c of FIG. 5C. In an embodiment, side removable window component 5050c is substantially curved along its long axis, and is configured to cover a side portion of a tip section of an endoscope. In an embodiment, a flat depression 5028c is located in a surface 5051c of the side removable window component 5050c. A window or opening 5004c for a side optical lens assembly, optical windows 5006c, 5008c for illuminators, and side nozzle opening 5010c are placed in the flat depression 5028c. In various embodiments, the side removable window component 5050c comprises a surface area in a range of 30 to 85% of the total surface area of the cylindrical side wall 5029c of the tip cover 5000 and, in turn, the flat depression 5028c comprises a surface area in a range of 0.50 to 90% of the total surface area of the side removable component 5050c. In various embodiments, an aspect ratio of width to length of the side removable window component 5050c is in a range of 1:6 and an aspect ratio of width to length of the flat depression 5028c is in a range of 1:10. In various embodiments, when the side removable window component 5050c is in place on said main component 5030c, a distance from the windows 5004c, 5006c, 5008c of the removable window component 5050 to the underlying optical elements and/or LEDs is in a range of 0 to 3 millimeters, and any increment therein.

Figure 6A:
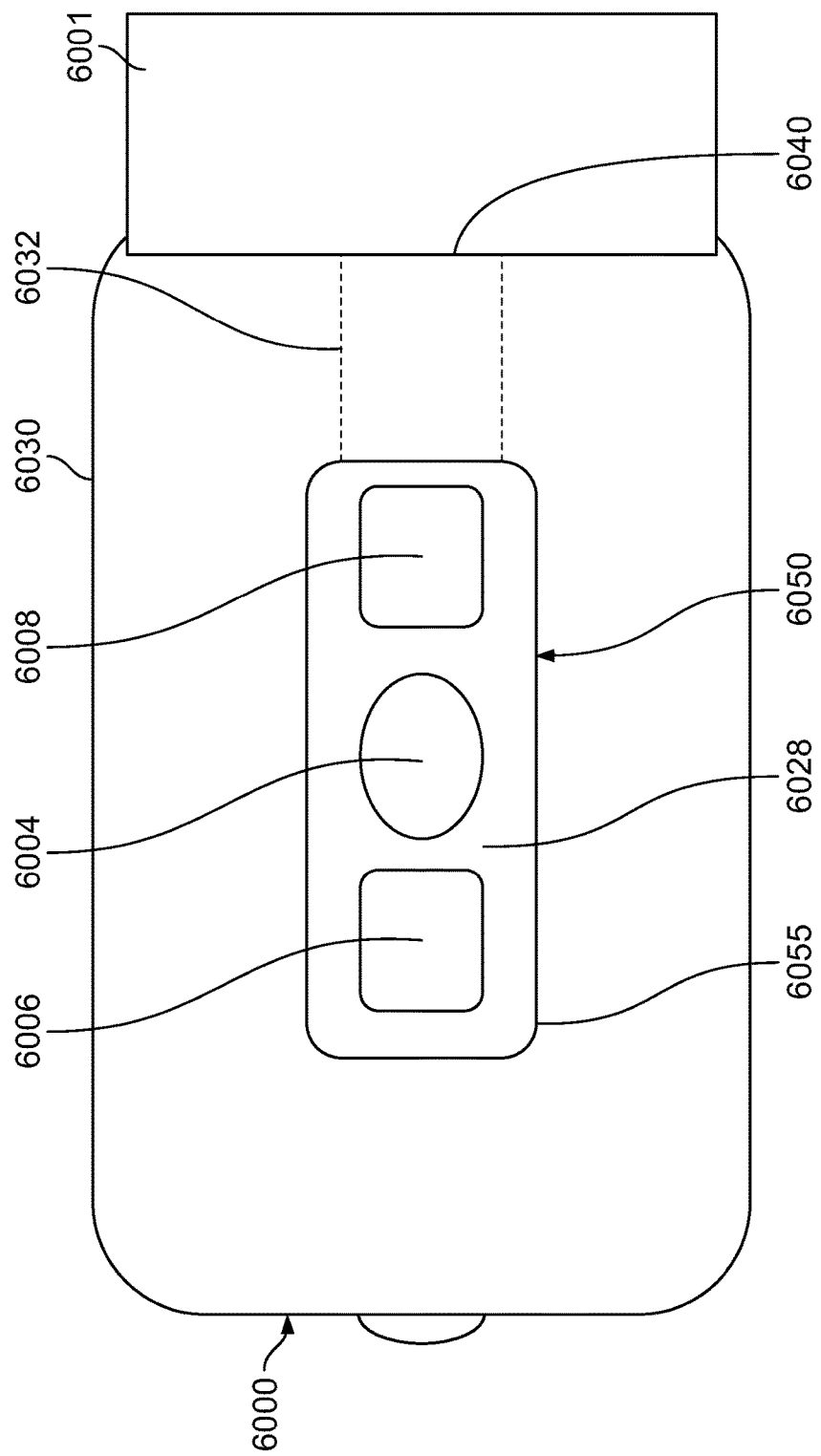
FIG. 6A illustrates another embodiment of a multi-element tip cover of the present specification.

FIG. 6A shows another embodiment of a multi-element tip cover 6000 of the present specification. Referring to FIG. 6A, tip cover 6000 includes a main component 6030. The main component 6030 of the tip cover 6000 is substantially cylindrical in an embodiment, and is configured to cover a major portion of the tip section 6001 of an endoscope. The main component 6030 of the tip cover further comprises a side window component 6050, located on a side surface 6055, also called the side wall. As mentioned earlier, the overall shape of the main component 6030 is substantially cylindrical, yet side components, including windows or openings, such as windows or openings 6004, 6006, 6008, for components such as the side camera, LEDs, and jet of the endoscope tip, are positioned in a flat depression 6028. This flat depression 6028 is located in the side window component 6050. The side window component 6050 is configured to cover a window opening (not shown) located on main component 6030, which is designed to provide access to the components (camera, LEDs, jet) in the inner part of the tip section.

In an embodiment, the main component 6030 further includes a groove 6032 on its side surface 6055 and complementary extensions off the sides of the removable window component that mate thereto. The groove 6032 is designed such that removable window component 6050 may be slid along groove 6032, longitudinally along a length of the endoscope tip, to expose the window opening and the components of the inner part of the endoscope tip when required. Thus, when one of the internal components of the tip section is to be repaired or replaced, the side window component 6050 is slid longitudinally along the groove 6032 to reveal the window opening, which provides access to the desired internal component. It should be appreciated that the groove could alternatively be on the removable window component 6050 and the mating members could be extending out from the main component 6030 into the window opening.

It may be noted that in an embodiment, a part of side window component 6050 has the form of an essentially flat surface which assists in directing the cleaning fluid injected from injector channel towards side optical assembly and optical windows. Lack of such a flat surface may result in dripping of the cleaning fluid along the curved surface of tip section of the endoscope without performing the desired cleaning action.

In an embodiment, windows or openings 6004, 6006, 6008 for the camera and illuminators of the endoscope tip (not shown in FIG. 6A) are located in notch or depression 6028. In this way, the outer windows (which are the outer lens of the side camera and side illuminators) located in the side wall and the side window component 6050 covering it are elevated from the depression in sidewall 6055, but still do not protrude from the level of cylindrical surface of the tip cover 6000. The notch/depression protects the sidewall and components thereof, such as side optical assembly, side illuminators, and side nozzle from both longitudinal and latitudinal mechanical shocks by keeping them below the level of the cylindrical surface of the tip cover 6000. In an embodiment, the outer windows and side nozzle are below the cylindrical surface of the tip cover, while the side window component 6050 is at the same level as the cylindrical surface of the tip cover. In an embodiment, the outer windows and side nozzle opening are positioned on the circumference of the endoscope tip at a distance (depth) ranging from approximately 1 to 9 millimeters from the surface of the tip, and in an embodiment are positioned at approximately 7.0 or 7.9 millimeters, from the surface of the tip.

In an embodiment, groove 6032 extends, alongside the surface 6055, from a proximal end of the side window component 6050 to the proximal end 6040 of the tip cover 6000, where the tip is connected to the endoscope tube. The side window component 6050 may be slid along said groove 6032, in a proximal direction, to move it away and reveal the window opening when required. Referring to FIG. 6A, the side window component 6050 is in a first position, slid most distally, and covers a window opening providing access to the components of the inner part of the endoscope tip. In an embodiment, the side window component 6050 includes a catching mechanism to prevent it from being completely removed from said tip cover 6000. In another embodiment, the side window component 6050 may be slid completely off of said main component 6030 and removed from said tip cover 6000. In other embodiments (not shown), a groove is positioned distal to the side window component, or above or below said side window component, when viewed from the side, to allow for sliding of the side window component in a distal, up, or down direction respectively to expose the components of the inner part of the endoscope tip.

Figure 6B:
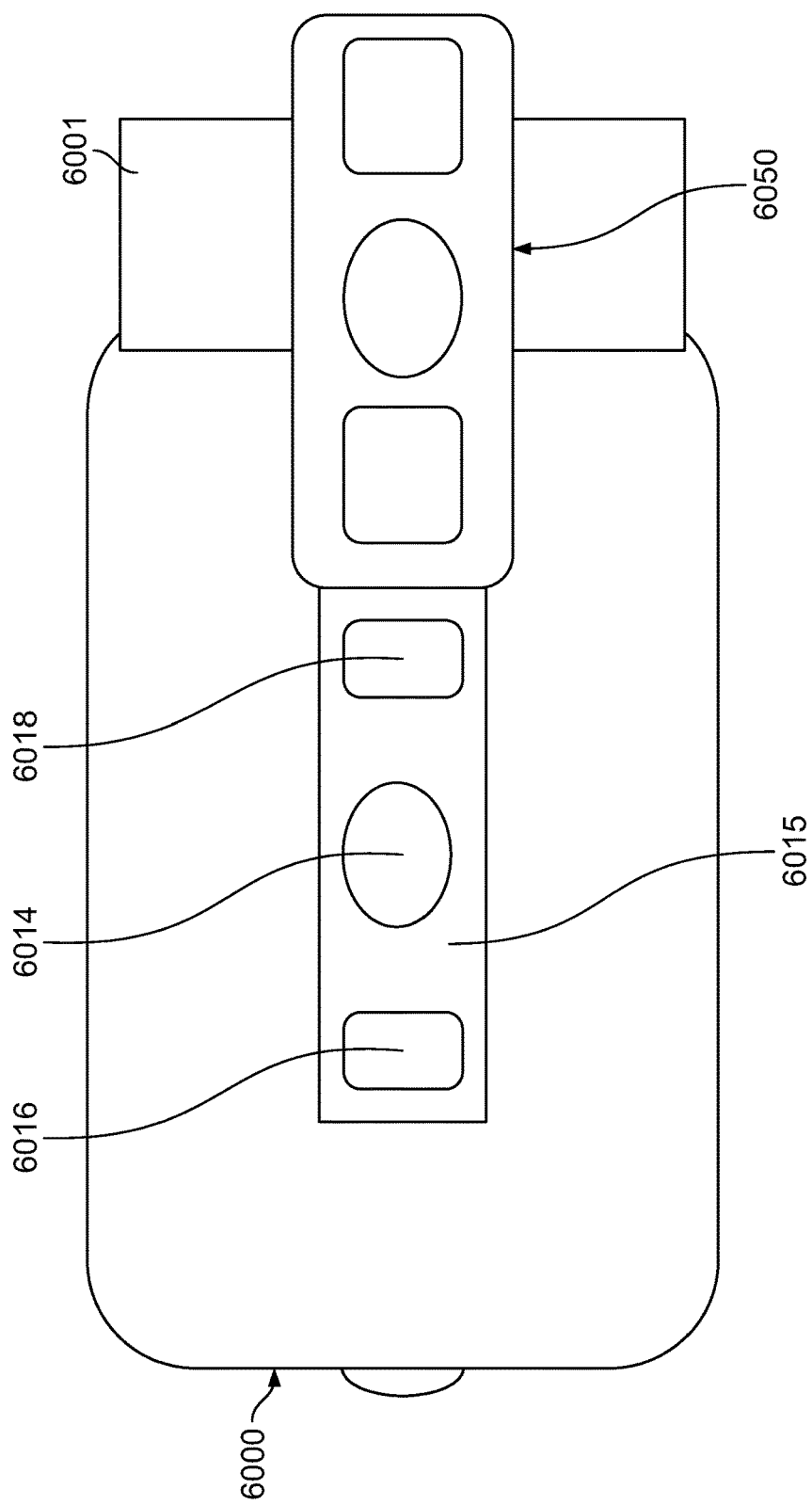
FIG. 6B illustrates the tip cover of FIG. 6A with a side window component slid proximally to a second position in accordance with an embodiment of the present specification.

FIG. 6B shows the tip cover 6000 of FIG. 6A with the side window component 6050 slid proximally to a second position. In FIG. 6B, the side window component 6050 is in its most proximal position, exposing window opening 6015 and providing access to components, such as a side camera 6014 and side illuminators 6016, 6018, of the inner part of the endoscope tip 6001.

Figure 6C:
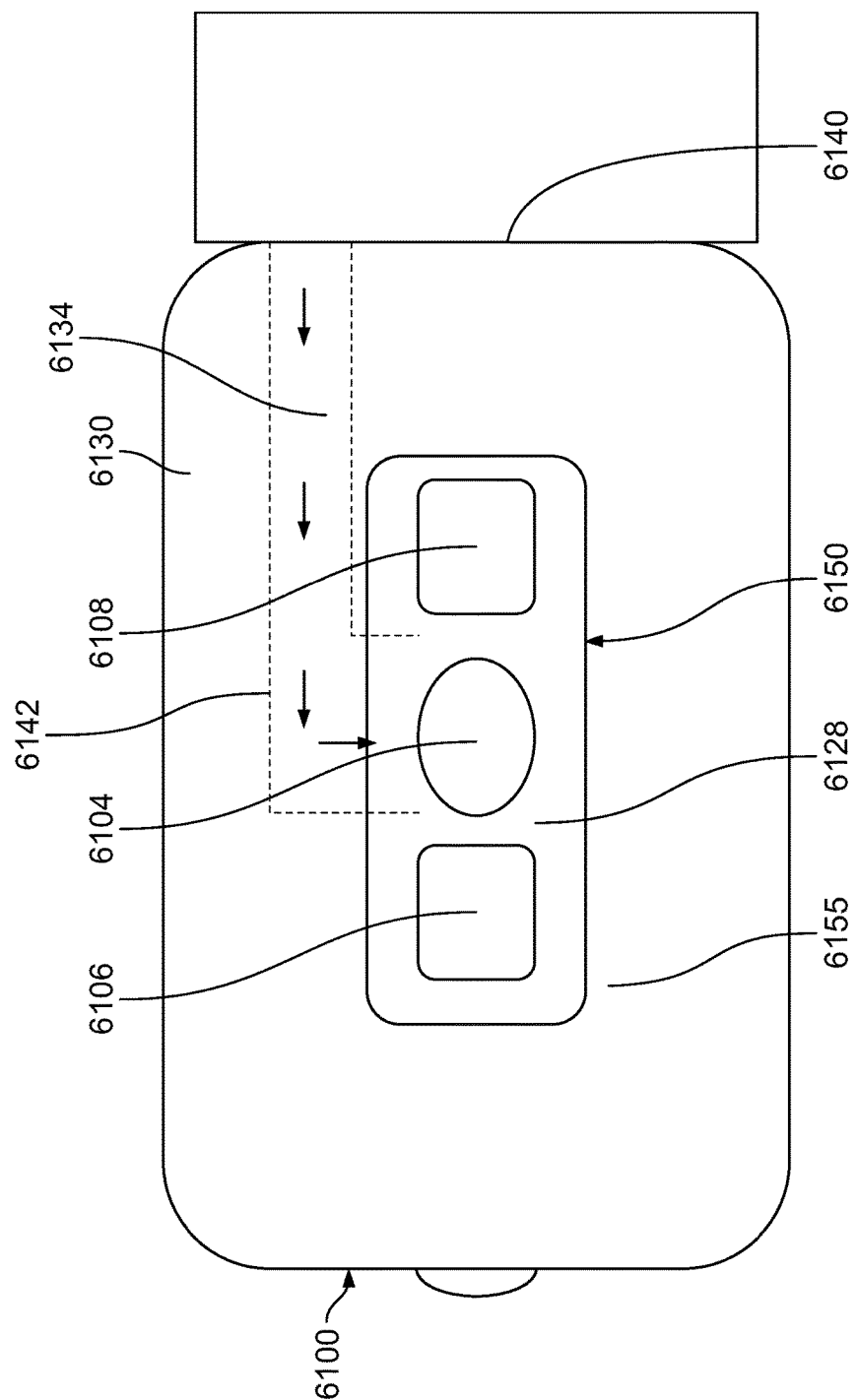
FIG. 6C illustrates yet another embodiment of a multi-element tip cover of the present specification.

FIG. 6C shows yet another embodiment of a multi-element tip cover 6100 of the present specification. Referring to FIG. 6C, the main component 6130 of the tip cover further includes a groove 6134 on its side surface 6155. In this embodiment, the groove 6134 is substantially "L" shaped and extends from the location 6142 of a side window component 6150 on the side surface 6155 to the proximal end 6140 of the tip cover 6100, where the tip is connected to the endoscope tube. The groove 6134 is designed such that removable window component 6150 may be slid along groove 6134 to expose a window opening (not shown) when required. Thus, when one of the internal components of the tip section is to be repaired or replaced, the side window component is moved along the groove 6134 to reveal the window opening, which provides access to the desired internal component.

In this embodiment, the removable window component 6150 located in the side wall 6155 is aligned with the outer surface of main component 6130 which is typically a substantially cylindrical surface. Side camera outer window 6104, illuminators outer windows 6106, 6108 and nozzle (not shown) are located in a depression 6128 in the removable window component 6150, such that they do not protrude from the level of cylindrical surface of the tip cover 6100.

Figure 7:
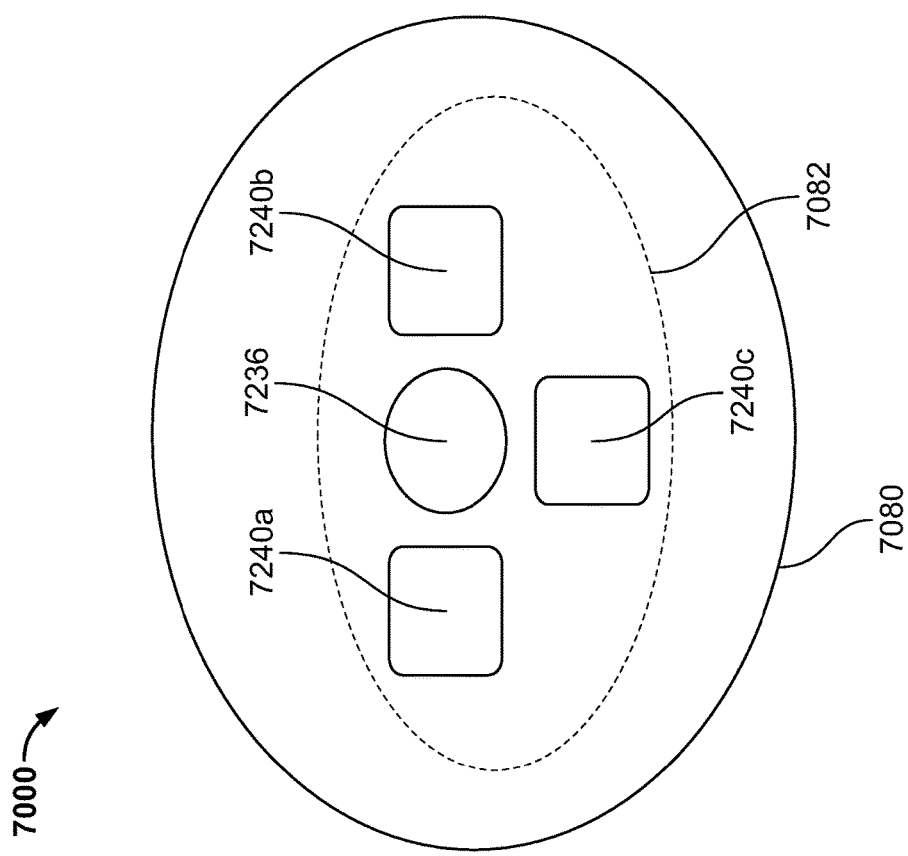
FIG. 7 illustrates a front face part of a multi-element tip cover in accordance with an embodiment of the present specification.

FIG. 7 shows another embodiment of a front face part 7080 of a multi-element tip cover 7000 of the present specification. Referring to FIG. 7, front face part 7080 includes windows 7240a, 7240b, and 7240c for the illuminators of the viewing element and window 7236 for the viewing element camera. The front face part 7080 of the tip cover 7000 further includes a front removable window component 7082 which is configured to allow access to the inner part of tip section located on a front panel (shown as 1102 in FIG. 4A). In embodiments, the window component 7082 can be removed, if required, without removing the remainder of the tip cover 7000. This allows repairing or replacing one of the several components of front panel 1102 shown in FIG. 4A, such as LEDs 1240a, 1240b, 1240c, optical element 1236, or any other element, without removing the remainder of the cover 7000 and preventing any potential damage to the packing and sealing of the tip section. In an embodiment, the front panel comprises a window opening that has edges for coupling to the front removable window component 7082, in the same manner as a side panel window opening couples to the side removable window component (shown as 5050c and explained with reference to FIGS. 5C-5E). In various embodiments, the front removable window component 7082 comprises a surface area in a range of 20 to 85% of the total surface area of the front face part 7080 of the tip cover 7000. In various embodiments, an aspect ratio of width to length of the front removable window component 7082 is in a range of 1:6. In various embodiments, when the removable window component 7082 is in place on said front face part 7080, the windows 7236, 7240a, 7240b, and 7240c of the front removable window component 7082 and the underlying optical elements and/or LEDs are aligned such that a distance from the windows 7236, 7240a, 7240b, and 7240c of the removable window component 7082 to the underlying optical elements and/or LEDs is in a range of 0 to 3 millimeters, and any increment therein.

In various embodiments, side window components 6050 and 6150 of FIG. 6A and FIG. 6C respectively are coupled to the multi-element tip cover by any of the various methods known in the art such as by using epoxy glue, ultrasonic welding or laser welding. In various embodiments, front window removable component 7082 of FIG. 7 is coupled to a front panel window opening of the multi-element tip cover by any suitable sealing or coupling means know in the art, such as but not limited to screws, hinges, hooks, adhesives, or welding.

Figure 8:
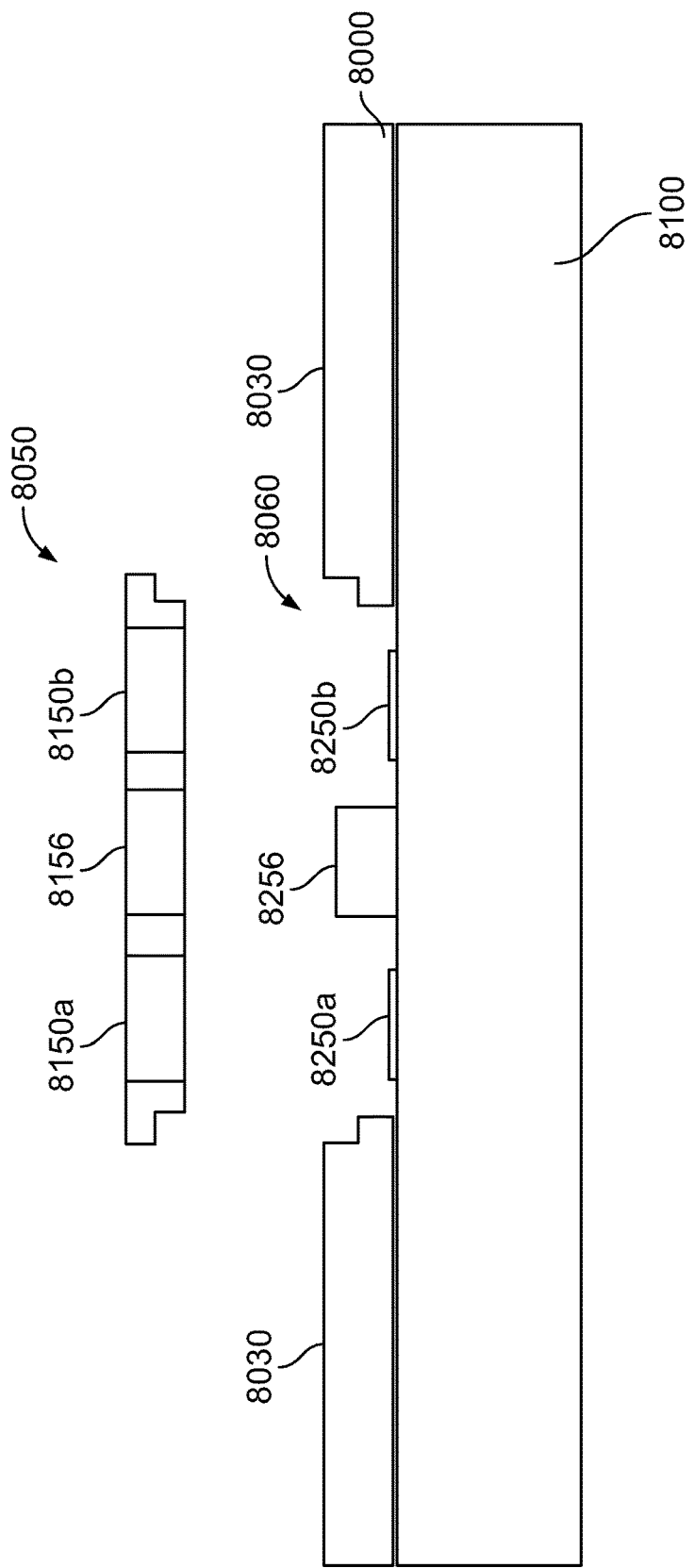
FIG. 8 illustrates a cross sectional view of a multi-element tip cover, when placed over an endoscope tip, according to an embodiment of the present specification.

FIG. 8 illustrates a partial side cross sectional view of multi-element tip cover 8000, when placed over an endoscope tip in accordance with an embodiment of the present specification. It may be noted that this figure represents part of the side panel of the tip, and does not show the front panel and the proximal part of the tip. Referring to FIG. 8, the inner part 8100 of an endoscope tip comprises a viewing element 8256 and its associated illuminators 8250a and 8250b. The endoscope tip is surrounded by the tip cover 8000, with the main component 8030 of the tip cover covering a major portion of the tip. A window opening 8060 is provided in the main component 8030, which provides access to the viewing element 8256, illuminators 8250a, 8250b and other components (not shown) in the inner part 8100 of the tip. As explained earlier with reference to FIGS. 5C-5E, a side removable window component 8050 is provided such that it covers the window opening 8060 in the main component 8030. In an embodiment, the side removable window component 8050 further comprises windows or openings such as the windows 8156, 8150a, 8150b corresponding to the viewing element 8256, illuminators 8150a, 8150b, and other components in the inner part. Thus, removable window component 8050 comprises a window 8156 corresponding to the viewing element 8256, and windows 8150a and 8150b corresponding to the illuminators 8250a and 8250b, respectively.

In an embodiment, side removable window component 8050 is produced by insertion molding of illuminators windows 8150a and 8150b and the outer window 8156 of viewing element 8256. In an embodiment, instead of a window 8156, the lens of the viewing element is molded into the side removal window component 8050. It may be appreciated that the location of the optical windows (8156, 8150a and 8150b) in the side removable window component 8050 is designed to align with the location of the viewing element and the illuminators (8256, 8250a and 8250b, respectively) of the inner part 8100 of the tip section.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A multi-component cover for a tip section of a multi-viewing element endoscope, said tip section comprising a front pointing viewing element and at least one side pointing viewing element, wherein each viewing element comprises an image sensor and a lens assembly, and each viewing element is associated with a discrete illuminator, said multi-component cover comprising:
    a main component configured to cover a portion of said tip section, said main component comprising a distal face and one or more side walls extending proximally from said distal face and extending longitudinally along a length of the tip section; and
    a removable window component located on the one or more side walls of said main component, said removable window component configured to removably cover a window opening located on said main component, wherein the optical axis of the front pointing viewing element and the optical axis of the at least one side pointing viewing element do not extend through the window opening, wherein said window opening is positioned to allow access to an inner part of said tip section without removing said main component.

2. The multi-component cover of claim 1, wherein said window opening is located on the main component such that it aligns with said removable window component.

3. The multi-component cover of claim 1, wherein said window opening has edges that are adapted to couple to the removable window component.

4. The multi-component cover of claim 1, wherein said window opening is aligned with at least one of:
    said side pointing viewing element;
    an optical assembly of said side pointing viewing element;
    a side discrete illuminator; and
    a side nozzle.

5. The multi-component cover of claim 4, wherein said window opening is aligned such that a distance from said window opening to the underlying side pointing viewing element, the underlying optical assembly, the underlying side nozzle, or the underlying side discrete illuminator is in a range of 0 to 3 millimeters.

6. The multi-component cover of claim 1, wherein the removable window component is a first removable window component, and wherein the multi-component cover further comprises a second removable window component positioned on a front end of the main component of said tip cover, said second removable window component being configured to cover a front window opening which allows access to a front inner part of said tip section.

7. The multi-component cover of claim 6, wherein said second removable window component comprises a window for at least one of:
    said front pointing viewing element;
    an optical assembly of said front pointing viewing element;
    a front discrete illuminator;
    a working/service channel;
    a front nozzle; and
    a front jet.

8. The multi-component cover of claim 7, wherein said window of the second removable window component is aligned such that a distance from said window of the second removable window component to the front pointing viewing element or front discrete illuminator is in a range of 0 to 3 millimeters.

9. The multi-component cover of claim 1, wherein the main component further includes a groove on one of the one or more side walls, said groove being configured to allow the removable window component to slide along the groove and be repositioned on, or removed from, the multi-component cover.

10. The multi-component cover of claim 1, wherein the removable window component comprises a flat surface to assist in directing a cleaning fluid injected from an injector channel towards a side optical assembly and one or more optical windows.

11. The multi-component cover of claim 1, wherein said tip section has a diameter of 17 mm or less.

12. The multi-component cover of claim 1, wherein said main component is cylindrical in shape and has a diameter ranging between 2 mm and 17 mm.

13. The multi-component cover of claim 1, wherein said removable window component comprises a flat depression having openings for accessing a side optical lens assembly, side illuminators and a side nozzle.

14. The multi-component cover of claim 1, wherein said window opening is positioned on a circumference of said main component at a distance of 1 to 9 mm from the distal face of said main component.

15. The multi-component cover of claim 1, wherein said window opening is positioned on a circumference of said main component at a distance of 7 mm to 7.9 mm from the distal face of said main component.

16. A tip section of a multi-camera endoscope, the tip section comprising:
 a front looking camera;
 a first side looking camera;
 an electronic circuit board coupled to at least one of the front looking camera and the first side looking camera; and
 a multi-component cover configured to cover said tip section, the multi-component cover comprising:
  a main component configured to cover at least a portion of said tip section; and
  a first side removable component coupled to a side surface portion of said main component, wherein said first side removable component is configured to removably cover an opening located on said main component, wherein the optical axis of the front looking camera and the optical axis of the first side looking camera do not extend through the opening, wherein said opening provides an unobstructed pathway between an area exterior to the tip section and the electronic circuit board when the first side removable component is removed from the opening, and wherein said opening is positioned to allow access to an inner part of said tip section without removing said main component.

17. The tip section of claim 16, wherein said tip section further comprises a second side looking camera, and said multi-component cover further comprises a second side removable component coupled to a side surface portion of said main component on an opposite side of said first side removable component, wherein said second side removable component is configured to cover a second opening located on said main component, wherein said second opening is configured to allow access to an inner part of said tip section without removing said main component, further wherein, when said first and second side removable components are in place on said main component, a distance from said first side removable component and said second side removable component to said first side looking camera and said second side looking camera, respectively, is in a range of 0 to 3 millimeters.

18. The tip section of claim 16 wherein said multi-component cover further comprises a front removable component configured to cover an opening located on a front portion of said main component and wherein said opening on the front portion is configured to allow access to the inner part of the tip section without removing said main component, wherein when said front removable component is in place on said main component, a distance from the front removable component to said front looking camera is in a range of 0 to 3 millimeters.

19. The tip section of claim 16, wherein said main component comprises a channel alongside said side removable component, and said side removable component is configured to be longitudinally pushed and slid through said channel to be repositioned in an open position in which the inner parts of the tip section can be accessed through said opening.

20. A multi-component cover for the a tip section of an endoscope, said tip section comprising at least one of a front pointing viewing element and a side pointing viewing element, wherein the at least one of a front pointing viewing element and a side pointing viewing element comprises an image sensor, said multi-component cover comprising:
 a main component configured to cover a portion of said tip section, said main component comprising a distal face and one or more side walls extending proximally from said distal face and extending longitudinally along a length of the tip section; and
 a removable window component located on the one or more side walls of said main component, said removable window component configured to removably cover a window opening located on said main component, wherein the optical axis of the at least one of a front pointing viewing element and the side pointing viewing element does not extend through the window opening, wherein said window opening is positioned to allow access to an inner part of said tip section without removing said main component.

* * * * *